(12) United States Patent
Fayol et al.

(10) Patent No.: US 9,073,914 B2
(45) Date of Patent: Jul. 7, 2015

(54) SUBSTITUTED ALKYL PYRIMIDIN-4-ONE DERIVATIVES

(75) Inventors: Aude Fayol, Paris (FR); Alistair Lochead, Paris (FR); Mourad Saady, Paris (FR); Julien Vache, Paris (FR); Philippe Yaiche, Paris (FR)

(73) Assignees: SANOFI, Paris (FR); MITSUBISHI TANABE PHARMA CORPORATION, Osaka (JP)

( * ) Notice: Subject to any disclaimer, the term of this patent is extended or adjusted under 35 U.S.C. 154(b) by 1209 days.

(21) Appl. No.: 12/968,868

(22) Filed: Dec. 15, 2010

(65) Prior Publication Data

US 2011/0144092 A1    Jun. 16, 2011

Related U.S. Application Data

(63) Continuation of application No. PCT/IB2009/006568, filed on Jun. 25, 2009.

(30) Foreign Application Priority Data

Jun. 26, 2008   (EP) .................................... 08290615

(51) Int. Cl.
| | |
|---|---|
| A01N 43/90 | (2006.01) |
| A61K 31/519 | (2006.01) |
| C07D 487/00 | (2006.01) |
| C07D 239/70 | (2006.01) |
| C07D 471/04 | (2006.01) |
| A61K 31/517 | (2006.01) |
| C07D 487/04 | (2006.01) |

(52) U.S. Cl.
CPC ............ *C07D 471/04* (2013.01); *A61K 31/519* (2013.01); *A61K 31/517* (2013.01); *C07D 487/04* (2013.01)

(58) Field of Classification Search
None
See application file for complete search history.

(56) References Cited

U.S. PATENT DOCUMENTS

| | | | |
|---|---|---|---|
| 4,104,386 | A | 8/1978 | Barreau et al. |
| 4,406,897 | A | 9/1983 | Campbell et al. |
| 4,461,769 | A | 7/1984 | Hermecz et al. |
| 4,804,663 | A | 2/1989 | Kennis et al. |
| 2005/0009843 | A1 | 1/2005 | Nakayama et al. |
| 2011/0136828 | A1 | 6/2011 | Lochead et al. |
| 2011/0144114 | A1 | 6/2011 | Lochead et al. |
| 2011/0144132 | A1 | 6/2011 | Fayol et al. |
| 2011/0144133 | A1 | 6/2011 | Lochead et al. |
| 2011/0144138 | A1 | 6/2011 | Lochead et al. |

FOREIGN PATENT DOCUMENTS

| | | |
|---|---|---|
| DE | 2705582 | 8/1977 |
| EP | 1136484 | 9/2001 |
| EP | 1454909 | 9/2004 |
| EP | 1460076 | 9/2004 |
| EP | 1790649 | 5/2007 |
| FR | 2413389 | 7/1979 |
| JP | 51070780 | 6/1976 |
| WO | WO 96/14844 | 5/1996 |
| WO | WO 97/16430 | 5/1997 |
| WO | WO 98/47876 | 10/1998 |
| WO | WO 02/087589 | 11/2002 |
| WO | WO 03/027115 | 4/2003 |
| WO | WO 2004/016607 | 2/2004 |
| WO | WO 2007/057790 | 5/2007 |

OTHER PUBLICATIONS

U.S. Appl. No. 12/968,927, filed Dec. 15, 2010, Almario Garcia, et al.
Pyrimido [1,2-a] Benzimidazol-4(10H)-one, 2-(4-Pyridinyl)-, Database Accession No. 2049193492, kcd-815548; abstract Aurora Screening Library (2008).
Brat, R.V., et. al., Glycogen Synthase Kinase 3: A Drug Target for CNS Therapies, Journal of Neurochemistry. vol. 89, pp. 1313-1317 (2004).
Carmichael, et al., Glycogen Synthase Kinase-3β Inhibitors Prevent Cellular Polyglutamine Toxicity Caused by the Huntington's Disease Mutation, The Journal of Biological Chemistry, 2002 (277)37 pp. 33791-33798.
Cohen, et al., GSK3 Inhibitors: Development and Therapeutic Potential, Nature Reviews, 2004 (3) pp. 479-487.
Droucheau, et al., *Plasmodium falciparum* Glycogen Synthase Kinase-3: Molecular Model, Expression, Intracellular Localisation and Selective Inhibitors, Biochimica et Biophysica Acta, 2004 (1897) pp. 181-196.

(Continued)

*Primary Examiner* — Jeffrey H Murray
(74) *Attorney, Agent, or Firm* — Morrison & Foerster LLP

(57) ABSTRACT

A pyrimidone derivative represented by formula (I) or a salt thereof, or a solvate thereof or a hydrate thereof:

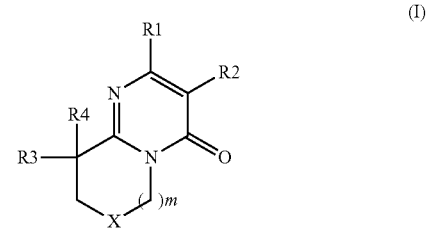

(I)

wherein X, R1, R2, R3, R4, and m are defined in the disclosure. Also disclosed are methods of preparing the compounds of formula (I), intermediates thereof and their use in therapeutics.

11 Claims, No Drawings

(56) References Cited

OTHER PUBLICATIONS

Dunbar, P. G., et al., Design, Synthesis and Neurochemical Evaluation of 2-Amino-5-(Alkoxycarbonyl)-3,4,5,6-Tetrahydropyridines and 2-Amino-5-(Alkoxycarbonyl)-1,4,5,6-Tetrahydropyrimidines as M1 Muscarinic Receptor Agonists, J. Med Chem., (1994). vol. 37, pp. 2774-2782.
Griffin, R. J., et al., Selective Benzopyranone and Pyrimido[2,1-a]Isoquinolin-4-one Inhibitors of DNA-Dependent Protein Kinase: Synthesis, Structure-Activity Studies, and Radiosensitization of a Human Tumor Cell Line in Vitro, J. Med. Chem., (2005), vol. 48, pp. 569-585.
Hansen, D. W., et. al., 2-Iminohomopiperidinium Salts as Selective Inhibitors of Inducible Nitric Oxide Synthase (INOS), J. Med. Chem., (1998), vol. 41, pp. 1361-1366.
Ishikawa, et al., Cyclic Guanidines. IX. 1) Synthesis of 2-Amino-3,4-Dihydroquinazolines as Blood Platelet Aggregation Inhibitors 2), Chem. Pharm. Bull. vol. 28, No. 5, pp. 1357-1364, (1980).
Katritzky, A. R., et al., Convenient Preparation of Tert-Butyl B-(Protected Amino)Esters, J. Org. Chem., (2002), vol. 67, pp. 4957-4959.
Kihara, et al., Reaction of Biguanides and Related Compounds, XVI. Synthesis of s-Triazinones and Fused s-Triazinones by Carbonylation of Biguanides and Related Compounds With Diethyl Azodicarboxylate , J. Heterocyclic Chem., vol. 27, pp. 1213-1216, (1990).
Kim, et al., Novel GSK-3B Inhibitors From Sequential Virtual Screening, Bioorganic & Medicinal Chemistry, vol. 16, (2008), pp. 636-643.
Koh, et al., Role of GSK-3B Activity in Motor Neuronal Cell Death Induced by G93A or A4V Mutant HSOD1 Gene, European Journal of Neuroscience, 2005 (22) pp. 301-309.
Li, C., et al., Pyridine Derivatives as Potent Inducers of Erythroid Differentiation in Friend Leukemia Cells, Journal of Medicinal Chemistry, vol. 21, No. 9, (1978). pp. 874-877.
Martinez, et al., Glycogen Synthase Kinase 3 (GSK-3) Inhibitors as New Promising Drugs for Diabetes, Neurodegeneration, Cancer, and Inflammation, Med. Res. Rev., 2002 (22)4 pp. 373-384.
Meijer, et al., Pharmacological Inhibitors of Glycogen Synthase Kinase 3, Trends in Pharmacological Sciences, 2004 (25)9 pp. 471-480.
Merour, et al., New Synthesis of (+/−)-2-Piperazinecarboxylic Acid, Tetrahedron Lett, 1991 (32) 22 pp. 2469-2470.
Obligado, et al., CDK/GSK-3 Inhibitors as Therapeutic Agents for Parenchymal Renal Diseases, Kidney Int'l, 2008 (73) pp. 684-690.
Perez, et al., Prion Peptide Induces Neuronal Cell Death Through a Pathway Involving Glycogen Synthase Kinase 3, Biochem. J., 2003 (372) pp. 129-136.
Sato, et al., Maintenance of Pluripotency in Human and Mouse Embryonic Stem Cells Through Activation of Wnt Signaling by a Pharmacological GSK-3-Specific Inhibitor, Nature Medicine, 2004 (10) pp. 55-63.
Thenappan, et al., An Expedient Synthesis of A-Fluoro-B-Ketoesters, Tetrahedron Letters, 1989 (30) 45 pp. 6113-6116.
Van Der Velden, J. L. J., et. al., Glycogen Synthase Kinase 3B Suppresses Myogenic Differentiation Through Negative Regulation of NFATc3, The Journal of Biological Chemistry, vol. 283, No. 1, pp. 358-366, (2008).
Von Angerer, et al., Product Subclass 3: 1,3,5-Triazines and Phosphorus Analogues, Science of Synthesis, Category 2: Hetarenes and Related Ring Systems Six-Membered Hetarenes with Two Unlike or More Than Two Heteroatoms and Fully Unsaturated Larger-Ring Heterocycles: Methods of Molecular Transformations, vol. 17 (2004), pp. 449-583.
Woodgett, Use of Peptide Substrates for Affinity Purification of Protein-Serine Kinases, Analytical Biochem., 1989 (180) pp. 237-241.
International Search Report for WO2009/156864 dated Dec. 30, 2009.

SUBSTITUTED ALKYL PYRIMIDIN-4-ONE DERIVATIVES

This application is a continuation of International Application No. PCT/IB2009/006568, filed Jun. 25, 2009, which is incorporated herein by reference in its entirety; which claims the benefit of priority of European Patent Application No. 08290615.7 filed Jun. 26, 2008.

TECHNICAL FIELD

The present invention relates to compounds that are useful as an active ingredient of a medicament for preventive and/or therapeutic treatment of neurodegenerative diseases caused by abnormal activity of GSK3β.

BACKGROUND ART

GSK3β (glycogen synthase kinase 3β) is a proline directed serine, threonine kinase that plays an important role in the control of metabolism, differentiation and survival. It was initially identified as an enzyme able to phosphorylate and hence inhibit glycogen synthase. It was later recognized that GSK3β was identical to tau protein kinase 1 (TPK1), an enzyme that phosphorylates tau protein in epitopes that are also found to be hyperphosphorylated in Alzheimer's disease and in several tauopathies.

Interestingly, protein kinase B (AKT) phosphorylation of GSK3β results in a loss of its kinase activity, and it has been hypothesized that this inhibition may mediate some of the effects of neurotrophic factors. Moreover, phosphorylation by GSK3β of β-catenin, a protein involved in cell survival, results in its degradation by an ubiquitinilation dependent proteasome pathway.

Thus, it appears that inhibition of GSK3β activity may result in neurotrophic activity. Indeed there is evidence that lithium, an uncompetitive inhibitor of GSK3β, enhances neuritogenesis in some models and also increases neuronal survival, through the induction of survival factors such as Bcl-2 and the inhibition of the expression of proapoptotic factors such as p53 and Bax.

Recent studies have demonstrated that β-amyloid increases the GSK3β activity and tau protein phosphorylation. Moreover, this hyperphosphorylation as well as the neurotoxic effects of β-amyloid are blocked by lithium chloride and by a GSK3β antisense mRNA. These observations strongly suggest that GSK3β may be the link between the two major pathological processes in Alzheimer's disease: abnormal APP (Amyloid Precursor Protein) processing and tau protein hyperphosphorylation.

Although tau hyperphosphorylation results in a destabilization of the neuronal cytoskeleton, the pathological consequences of abnormal GSK3β activity are, most likely, not only due to a pathological phosphorylation of tau protein because, as mentioned above, an excessive activity of this kinase may affect survival through the modulation of the expression of apoptotic and antiapoptotic factors. Moreover, it has been shown that β-amyloid-induced increase in GSK3β activity results in the phosphorylation and, hence the inhibition of pyruvate dehydrogenase, a pivotal enzyme in energy production and acetylcholine synthesis.

Altogether these experimental observations indicate that GSK3β may find application in the treatment of the neuropathological consequences and the cognitive and attention deficits associated with Alzheimer's disease, as well as other acute and chronic neurodegenerative diseases and other pathologies where GSK3β is deregulated (Nature reviews Vol. 3, June 2004, p. 479-487; Trends in Pharmacological Sciences Vol. 25 No. 9, September 2004, p. 471-480; Journal of neurochemistry 2004, 89, 1313-1317; Medicinal Research Reviews, Vol. 22, No. 4, 373-384, 2002).

The neurodegenerative diseases include, in a non-limiting manner, Parkinson's disease, tauopathies (e.g. Fronto temporal dementia, corticobasal degeneration, Pick's disease, progressive supranuclear palsy), Wilson's disease, Huntington's disease (The Journal of biological chemistry Vol. 277, No. 37, Issue of September 13, pp. 33791-33798, 2002), Prion disease (Biochem. J. 372, p. 129-136, 2003) and other dementia including vascular dementia; acute stroke and other traumatic injuries; cerebrovascular accidents (e.g. age related macular degeneration); brain and spinal cord trauma; amyotrophic lateral sclerosis (European Journal of Neuroscience, Vol. 22, pp. 301-309, 2005) peripheral neuropathies; retinopathies and glaucoma. Recent studies have also shown that inhibition of GSK3β results in neuronal differentiation of embryonic stem cells (ESC) and support the renewal of human and mouse ESCs and the maintenance of their pluripotency. This suggests that inhibitors of GSK3β could have applications in regenerative medicine (Nature Medicine 10, p. 55-63, 2004).

Inhibitors of GSK3β may also find application in the treatment of other nervous system disorders, such as bipolar disorders (manic-depressive illness). For example lithium has been used for more than 50 years as a mood stabilizer and the primary treatment for bipolar disorder. The therapeutic actions of lithium are observed at doses (1-2 mM) where it is a direct inhibitor of GSK3β. Although the mechanism of action of lithium is unclear, inhibitors of GSK3β could be used to mimic the mood stabilizing effects of lithium. Alterations in Akt-GSK3β signaling have also been implicated in the pathogenesis of schizophrenia.

In addition, inhibition of GSK3β could be useful in treating cancers, such as colorectal, prostate, breast, non-small cell lung carcinoma, thyroid cancer, T or B-cell leukaemia and several virus-induced tumours. For example, the active form of GSK3β has been shown to be elevated in the tumors of colorectal cancer patients and inhibition of GSK3β in colorectal cancer cells activates p53-dependent apoptosis and antagonises tumor growth. Inhibition of GSK3β also enhances TRAIL-induced apoptosis in prostate cancer cell lines. GSK3β also plays a role in the dynamics of the mitotic spindle and inhibitors of GSK3β prevent chromosome movement and lead to a stabilization of microtubules and a prometaphase-like arrest that is similar to that observed with low doses of Taxol. Other possible applications for GSK3β inhibitors include therapy for non-insulin dependent diabetes (such as diabetes type II), obesity and alopecia.

Inhibitors of human GSK3β may also inhibit pfGSK3, an ortholog of this enzyme found in *Plasmodium falciparum*, as a consequence they could be used for the treatment of malaria (Biochimica et Biophysica Acta 1697, 181-196, 2004).

Recently, both human genetics and animal studies have pointed out the role of Wnt/LPR5 pathway as a major regulator of bone mass accrual. Inhibition of GSK3β leads to the consequent activation of canonical Wnt signalling. Because deficient Wnt signalling has been implicated in disorders of reduced bone mass, GSK3β inhibitors may also be used for treating disorders of reduced bone mass, bone-related pathologies, osteoporosis.

According to recent data, GSK3β inhibitors might be used in the treatment or prevention of *Pemphigus vulgaris*.

Recent studies show that GSK3beta inhibitor treatment improves neutrophil and megakaryocyte recovery. Therefore, GSK3beta inhibitors will be useful for the treatment of neutropenia induced by cancer chemotherapy.

Previous studies have shown that GSK3 activity decreases LTP, a electrophysiological correlate of memory consolidation, suggesting that inhibitor of this enzyme may have procognitive activity. Procognitive effects of the compound could find application for the treatment of memory deficits characteristic of Alzheimer's disease, Parkinson disease, age-associated memory impairment, mild cognitive impairment, brain trauma, schizophrenia and other conditions in which such deficits are observed.

Inhibitors of GSK3β may also find application in the treatment of parenchymal renal diseases (Nelson P J, Kidney International Advance online publication 19 Dec. 2007) and in the prevention or treatment of muscle atrophy (J. Biol. Chem. (283) 2008, 358-366).

DISCLOSURE OF THE INVENTION

An object of the present invention is to provide compounds useful as an active ingredient of a medicament for preventive and/or therapeutic treatment of a disease caused by abnormal GSK3β activity, more particularly of neurodegenerative diseases. More specifically, the object is to provide novel compounds useful as an active ingredient of a medicament that enables prevention and/or treatment of neurodegenerative diseases such as Alzheimer's disease.

Thus, the inventors of the present invention have identified compounds possessing inhibitory activity against GSK3β. As a result, they found that compounds represented by the following formula (I) had the desired activity and were useful as an active ingredient of a medicament for preventive and/or therapeutic treatment of the aforementioned diseases.

The present invention thus provides as an object of the invention the pyrimidone derivatives represented by the formula (I) or salts thereof:

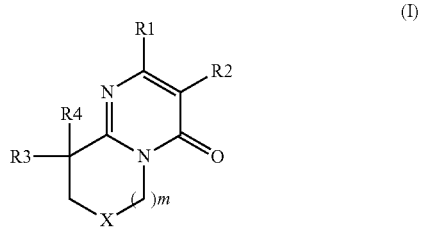

wherein:
X represents a methylene, NH, a nitrogen atom substituted by a C(O)—O—($C_{1-6}$-alkyl) group;
R1 represents a 2, 3 or 4-pyridine ring or a 2, 4 or 5-pyrimidine ring, the ring being optionally substituted by a $C_{1-6}$ alkyl group, a $C_{1-6}$ alkoxy group or a halogen atom;
R2 represents a hydrogen atom, a $C_{1-6}$ alkyl group or a halogen atom;
R3 represents a $C_{1-6}$ alkyl group this $C_{1-6}$ alkyl group being optionally substituted by 1 to 4 substituents selected from a halogen atom, a hydroxyl group, a $C_{1-6}$ alkoxy group, a $C_{1-2}$ perhalogenated alkyl group, a $C_{1-3}$ halogenated alkyl group, $C_{1-6}$ alkyl group, an aromatic group and the aromatic group being optionally substituted by 1 to 4 substituents selected from a halogen atom, a hydroxyl group, a $C_{1-6}$ alkoxy group, a $C_{1-6}$ alkyl group;
R4 represents a hydrogen atom, a halogen atom, a hydroxyl group, a $C_{1-6}$ alkyl group;

m represents 1 to 2 when X is a methylene or
m represents 2 when X is NH, a nitrogen atom substituted by a C(O)—O—($C_{1-6}$-alkyl) group;
in the form of a free base or of an addition salt with an acid.

According to another aspect of the present invention, there is provided a medicament comprising as an active ingredient a substance selected from the group consisting of the pyrimidone derivatives represented by formula (I) and the physiologically acceptable salts thereof, and the solvates thereof and the hydrates thereof. As preferred embodiments of the medicament, there are provided the aforementioned medicament which is used for preventive and/or therapeutic treatment of diseases caused by abnormal GSK3β activity, and the aforementioned medicament which is used for preventive and/or therapeutic treatment of neurodegenerative diseases and in addition other diseases such as:

Non-insulin dependent diabetes (such as diabetes type II) and obesity; malaria, bipolar disorders (manic depressive illness); schizophrenia; alopecia or cancers such as colorectal, prostate, breast cancer, non-small cell lung carcinoma, thyroid cancer, T or B-cell leukaemia, several virus-induced tumours and bone related pathologies; the treatment of parenchymal renal diseases and in the prevention or treatment of muscle atrophy; the treatment of cognitive and memory deficit. The medicament could also find an application in regenerative medicine.

As further embodiments of the present invention, there are provided the aforementioned medicament wherein the diseases are neurodegenerative diseases and are selected from the group consisting of Alzheimer's disease, Parkinson's disease, tauopathies (e.g. Fronto temporal dementia, corticobasal degeneration, Pick's disease, progressive supranuclear palsy), Wilson's disease, Huntington's disease, Prion disease and other dementia including vascular dementia; acute stroke and others traumatic injuries; cerebrovascular accidents (e.g. age related macular degeneration); brain and spinal cord trauma; amyotrophic lateral sclerosis; peripheral neuropathies; retinopathies and glaucoma, and the aforementioned medicament in the form of pharmaceutical composition containing the above substance as an active ingredient together with one or more pharmaceutical additives.

As further embodiments of the present invention, there are provided the aforementioned medicament wherein the bones related pathologies are osteoporosis. The present invention further provides an inhibitor of GSK3β activity comprising as an active ingredient a substance selected from the group consisting of the pyrimidone derivatives of formula (I) and the salts thereof, and the solvates thereof and the hydrates thereof.

According to further aspects of the present invention, there is provided a method for preventive and/or therapeutic treatment of neurodegenerative diseases caused by abnormal GSK3β activity, which comprises the step of administering to a patient a preventively and/or therapeutically effective amount of a substance selected from the group consisting of pyrimidone derivatives of formula (I) and the physiologically acceptable salts thereof, and the solvates thereof and the hydrates thereof; and a use of a substance selected from the group consisting of the pyrimidone derivatives of formula (I) and the physiologically acceptable salts thereof, and the solvates thereof and the hydrates thereof for the manufacture of the aforementioned medicament.

As used herein, the $C_{x-t}$ group represents a group from x to t carbon atoms. The alkyl group represents a straight or branched or cyclo alkyl group optionally substituted by a straight, branched or cyclic $C_{1-6}$ alkyl group for example, methyl group, ethyl group, n-propyl group, isopropyl group, n-butyl group, isobutyl group, sec-butyl group, tert-butyl group, n-pentyl group, isopentyl group, neopentyl group, 1,1-dimethylpropyl group, n-hexyl group, isohexyl group, cyclopropylmethyl, cyclopropyl group, cyclopentyl group and the like;

The $C_{1-6}$ alkoxy group represents an alkyloxy group having 1 to 4 carbon atoms for example, methoxy group, ethoxy group, propoxy group, isopropoxy group, butoxy group, isobutoxy group, sec-butoxy group, tert-butoxy group, and the like;

The halogen atom represents a fluorine, chlorine, bromine or iodine atom;

The $C_{1-2}$ perhalogenated alkyl group represents an alkyl group wherein all the hydrogen atoms have been substituted by a halogen, for example a $CF_3$ or $C_2F_6$, The $C_{1-3}$ halogenated alkyl group represents an alkyl group wherein at least, one hydrogen has not been substituted by a halogen atom;

The aromatic ring represents a phenyl group or a naphthyl group;

A leaving group L represents a group which could be easily cleaved and substituted; such a group may be for example a tosyl, a mesyl, a bromide and the like.

The compounds represented by the aforementioned formula (I) may form a salt. Examples of the salts include, when an acidic group exists, salts of alkali metals and alkaline earth metals such as lithium, sodium, potassium, magnesium, and calcium; salts of ammonia and amines such as methylamine, dimethylamine, trimethylamine, dicyclohexylamine, tris(hydroxymethyl)aminomethane, N,N-bis(hydroxyethyl)piperazine, 2-amino-2-methyl-1-propanol, ethanolamine, N-methylglucamine, and L-glucamine; or salts with basic amino acids such as lysine, δ-hydroxylysine and arginine. The base-addition salts of acidic compounds are prepared by standard procedures well known in the art.

When a basic group exists, examples include salts with mineral acids such as hydrochloric acid, hydrobromic acid; salts with organic acids such as acetic acid, propionic acid, tartaric acid, fumaric acid, maleic acid, malic acid, oxalic acid, succinic acid, citric acid, benzoic acid and the like.

The acid-addition salts of the basic compounds are prepared by standard procedures well know in the art which include, but are not limited thereto, dissolving the free base in an aqueous alcohol solution containing the appropriate acid and isolating the salt by evaporating the solution, or by reacting the free base and an acid in an organic solvent, in which case the salt separates directly, or is precipitated with a second organic solvent, or can be obtained by concentration of the solution. The acids which can be used to prepare the acid-addition salts include preferably those which produce, when combined with the free base, pharmaceutically-acceptable salts, that is, salts whose anions are relatively innocuous to the animal organism in pharmaceutical doses of the salts, so that the beneficial properties inherent in the free base are not compromised by side effects ascribable to the anions. Although medicinally acceptable salts of the basic compounds are preferred, all acid-addition salts are within the scope of the present invention.

In addition to the pyrimidone derivatives represented by the aforementioned formula (I) and salts thereof, their solvates and hydrates also fall within the scope of the present invention.

The pyrimidone derivatives represented by the aforementioned formula (I) may have one or more asymmetric carbon atoms. As for the stereochemistry of such asymmetric carbon atoms, they may independently be either (R) or (S) configuration, and the derivative may exist as stereoisomers such as optical isomers, or diastereoisomers. Any stereoisomers in pure form, any mixtures of stereoisomers, racemates and the like fall within the scope of the present invention.

In a first embodiment of the invention, there is provided compounds wherein R1 represents an unsubstituted 4-pyridine ring or unsubstituted 4-pyrimidine ring, in the form of a free base or of an addition salt with an acid.

In a second embodiment of the invention, there is provided compounds of formula (I):

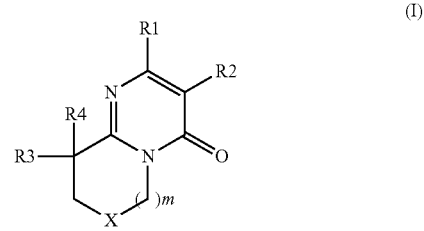

(I)

wherein:
X represents a methylene, NH, a nitrogen atom substituted by a C(O)—O—($C_{1-6}$-alkyl) group;
R1 represents an unsubstituted 4-pyridine ring or an unsubstituted 4-pyrimidine ring;
R2 represents a hydrogen atom;
R3 represents a $C_{1-6}$ alkyl group this $C_{1-6}$ alkyl group being optionally substituted by 1 to 4 substituents selected from a halogen atom, a hydroxyl group, a $C_{1-2}$ perhalogenated alkyl group, $C_{1-6}$ alkyl group, a phenyl group and the phenyl group being optionally substituted by 1 to 4 substituents selected from a halogen atom, a $C_{1-6}$ alkoxy group;
R4 represents a hydrogen atom;
m represents 1 to 2 when X is a methylene or
m represents 2 when X is NH, a nitrogen atom substituted by a C(O)—O—($C_{1-6}$-alkyl) group;
in the form of a free base or of an addition salt with an acid.

In a third embodiment of the invention, there is provided compounds of formula (I):

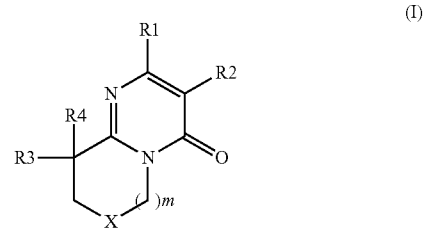

(I)

wherein:
X represents a methylene, NH, a nitrogen atom substituted by a C(O)—O—($C_{1-6}$-alkyl) group;
R1 represents an unsubstituted 4-pyridine ring or an unsubstituted 4-pyrimidine ring;
R2 represents a hydrogen atom;
R3 represents a $C_{1-6}$ alkyl group this $C_{1-6}$ alkyl group being optionally substituted by 1 to 4 substituents selected from a halogen atom, a hydroxyl group, a $C_{1-2}$ perhalogenated alkyl group, $C_{1-6}$ alkyl group, a phenyl group and the phenyl group being optionally substituted by 1 to 4 substituents selected from a halogen atom, a $C_{1-6}$ alkoxy group;
R4 represents a $C_{1-6}$ alkyl group;

m represents 1 to 2 when X is a methylene or m represents 2 when X is NH, a nitrogen atom substituted by a C(O)—O—(C$_{1-6}$-alkyl) group;

in the form of a free base or of an addition salt with an acid.

Examples of compounds of the present invention are shown in table 1 and table 2 hereinafter. However, the scope of the present invention is not limited by these compounds. The nomenclature is given according to IUPAC rules.

A further object of the present invention includes the group of compounds of table 1 of formula as defined hereunder:
1. (+/−)-9-[2-(2-Methoxy-phenyl)-ethyl]-2-pyridin-4-yl-6,7,8,9-tetrahydro-pyrido[1,2-α]pyrimidin-4-one
2. (+/−)-9-(3-Chloro-benzyl)-2-pyrimidin-4-yl-6,7,8,9-tetrahydro-pyrido[1,2-α]pyrimidin-4-one
3. (+/−)-9-(4-Fluoro-benzyl)-2-pyrimidin-4-yl-6,7,8,9-tetrahydro-pyrido[1,2-α]pyrimidin-4-one
4. (+/−)-9-(5-Bromo-2-methoxy-benzyl)-2-pyrimidin-4-yl-6,7,8,9-tetrahydro-pyrido[1,2-α]pyrimidin-4-one A further object of the present invention includes the group of compounds of table 2 of formula as defined hereunder:
1. (+/−)-10-Methyl-2-pyrimidin-4-yl-7,8,9,10-tetrahydro-6H-pyrimido[1,2-α]azepin-4-one
2. (+/−)-10-Methyl-2-pyridin-4-yl-7,8,9,10-tetrahydro-6H-pyrimido[1,2-α]azepin-4-one
3. (+/−)-10-Ethyl-2-pyrimidin-4-yl-7,8,9,10-tetrahydro-6H-pyrimido[1,2-α]azepin-4-one
4. (+/−)-10-Ethyl-2-pyridin-4-yl-7,8,9,10-tetrahydro-6H-pyrimido[1,2-α]azepin-4-one
5. (+/−)-10-(2-Phenyl-ethyl)-2-pyrimidin-4-yl-7,8,9,10-tetrahydro-6H-pyrimido[1,2-α]azepin-4-one
6. (+/−)-10-Benzyl-2-pyrimidin-4-yl-7,8,9,10-tetrahydro-6H-pyrimido[1,2-α]azepin-4-one
7. (+/−)-10-(3-Phenyl-propyl)-2-pyrimidin-4-yl-7,8,9,10-tetrahydro-6H-pyrimido[1,2-α]azepin-4-one
8. (+/−)-10-[(4-Fluoro-2-methoxy-phenyl)-hydroxy-methyl]-2-pyrimidin-4-yl-7,8,9,10-tetrahydro-6H-pyrimido[1,2-α]azepin-4-one
9. (+/−)-10-[2-(3,4-Dimethoxy-phenyl)-ethyl]-2-pyrimidin-4-yl-7,8,9,10-tetrahydro-6H-pyrimido[1,2-α]azepin-4-one
10. (+/−)-10-[Fluoro-(4-fluoro-2-methoxy-phenyl)-methyl]-2-pyrimidin-4-yl-7,8,9,10-tetrahydro-6H-pyrimido[1,2-α]azepin-4-one
11. (+/−)-10-[2-(4-Methoxy-phenyl)-ethyl]-2-pyrimidin-4-yl-7,8,9,10-tetrahydro-6H-pyrimido[1,2-α]azepin-4-one
12. (+/−)-10-[2-(2-Methoxy-phenyl)-ethyl]-2-pyrimidin-4-yl-7,8,9,10-tetrahydro-6H-pyrimido[1,2-α]azepin-4-one
13. (+/−)-10-(2-Methyl-2-phenyl-propyl)-2-pyrimidin-4-yl-7,8,9,10-tetrahydro-6H-pyrimido[1,2-α]azepin-4-one
14. (+/−)-10-Isobutyl-2-pyrimidin-4-yl-7,8,9,10-tetrahydro-6H-pyrimido[1,2-α]azepin-4-one
15. (+/−)-10-[2-(4-Fluoro-2-methoxy-phenyl)-ethyl]-2-pyrimidin-4-yl-7,8,9,10-tetrahydro-6H-pyrimido[1,2-α]azepin-4-one
16. (+/−)-10-[2-(2,4-Difluoro-phenyl)-ethyl]-2-pyrimidin-4-yl-7,8,9,10-tetrahydro-6H-pyrimido[1,2-α]azepin-4-one
17. (+/−)-10-(1-Hydroxy-2-phenyl-ethyl)-2-pyrimidin-4-yl-7,8,9,10-tetrahydro-6H-pyrimido[1,2-α]azepin-4-one
18. (+/−)-10-Cyclopentyl-2-pyrimidin-4-yl-7,8,9,10-tetrahydro-6H-pyrimido[1,2-α]azepin-4-one
19. (+/−)-10-(1-Fluoro-2-phenyl-ethyl)-2-pyrimidin-4-yl-7,8,9,10-tetrahydro-6H-pyrimido[1,2-α]azepin-4-one
20. (+/−)-10-Cyclopropyl-2-pyrimidin-4-yl-7,8,9,10-tetrahydro-6H-pyrimido[1,2-α]azepin-4-one
21. (+/−)-2-Pyrimidin-4-yl-10-[2,2,2-trifluoro-1-hydroxy-1-(4-methoxy-benzyl)-ethyl]-7,8,9,10-tetrahydro-6H-pyrimido[1,2-α]azepin-4-one
22. (+/−)-10-(1-Hydroxy-ethyl)-2-pyrimidin-4-yl-7,8,9,10-tetrahydro-6H-pyrimido[1,2-α]azepin-4-one
23. (+/−)-10-(1-Fluoro-ethyl)-2-pyrimidin-4-yl-7,8,9,10-tetrahydro-6H-pyrimido[1,2-α]azepin-4-one
24. (+/−)-10-(4-Fluoro-benzyl)-2-pyrimidin-4-yl-7,8,9,10-tetrahydro-6H-pyrimido[1,2-α]azepin-4-one
25. (+/−)-10-(1-Hydroxy-2-phenyl-ethyl)-10-methyl-2-pyrimidin-4-yl-7,8,9,10-tetrahydro-6H-pyrimido[1,2-α]azepin-4-one
26. (+)-10-(4-Fluoro-benzyl)-2-pyrimidin-4-yl-7,8,9,10-tetrahydro-6H-pyrimido[1,2-α]azepin-4-one
27. (−)-10-(4-Fluoro-benzyl)-2-pyrimidin-4-yl-7,8,9,10-tetrahydro-6H-pyrimido[1,2-α]azepin-4-one.

A further object of the present invention includes the group of compounds of table 3 of formula as defined hereunder:
1. (+/−)-9-Ethyl-4-oxo-2-pyrimidin-4-yl-5,6,8,9-tetrahydro-4H-1,4-a,7-triaza-benzocycloheptene-7-carboxylic acid ethyl ester
2. (+/−)-9-Ethyl-2-pyrimidin-4-yl-6,7,8,9-tetrahydro-5H-1,4-a,7-triaza-benzocyclohepten-4-one
3. (+/−)-9-(2-Phenyl-ethyl)-2-pyrimidin-4-yl-6,7,8,9-tetrahydro-5H-1,4-a,7-triaza-benzocyclohepten-4-one
4. (+/−)-9-(4-Fluoro-benzyl)-4-oxo-2-pyrimidin-4-yl-5,6,8,9-tetrahydro-4H-1,4-a,7-triaza-benzocycloheptene-7-carboxylic acid ethyl ester As a further object, the present invention concerns also methods for preparing the pyrimidone compounds represented by the aforementioned formula (I).

These compounds can be prepared, for example, according to methods explained below.

Preparation Method

Pyrimidone compounds represented by the aforementioned formula (I), may be prepared according to the method described in the scheme 1, starting from compound of formula (II). The conditions which may be used are given in the chemical examples.

Scheme 1

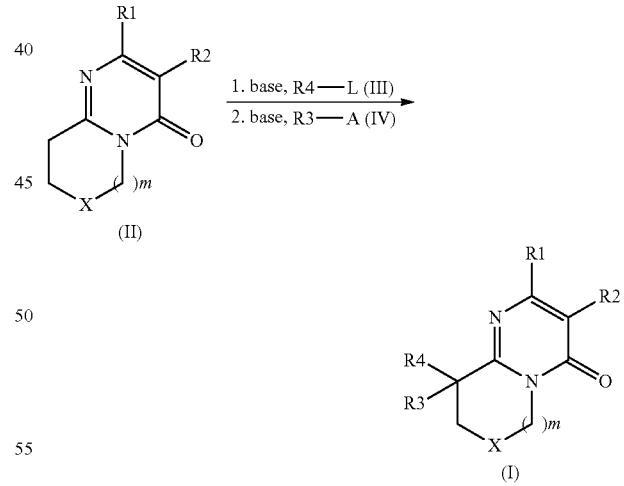

(In the above scheme, the definition of R1, R2, R3, R4, X and m are the same as already described, L represents a leaving group and A represents a suitable electrophilic group which allows the preparation of the pyrimidone derivative represented by the above formula (I)).

According to this method, the pyrimidone derivative represented by the above formula (II), wherein R1, R2, m and X are as defined for compound of formula (I), can be deprotonated with strong base such as sodium hydride, lithium bis (trimethylsilyl)amide, lithium diisopropyl amide, n-butyl lithium, tert-butyl lithium or sec-butyl lithium in a solvent such as ether, tetrahydrofuran, dimethylformamide and the resultant anion can react with a suitable electrophile. The resultant anion can react with a compound of formula (III) wherein R4 is defined for compound of formula (I) and L represents a leaving group which could be easily cleaved and substituted; such a group may be for example a tosyl, a mesyl, a bromide and the like. The resultant compound can be deprotonated a second time with strong base such as sodium hydride, lithium bis(trimethylsilyl)amide, lithium diisopropyl amide, n-butyl lithium, tert-butyl lithium or sec-butyl lithium in a solvent such as ether, tetrahydrofuran, dimethylformamide and the resultant anion can react with a suitable electrophile of formula (IV) wherein R3 and A are as defined are as defined above and below to afford the compound of the aforementioned formula (I).

Moreover, according to this method, the pyrimidone derivative represented by the above formula (II), wherein R1, R2, m and X are as defined for compound of formula (I), can be deprotonated with strong base such as sodium hydride, lithium bis(trimethylsilyl)amide, lithium diisopropyl amide, n-butyl lithium, tert-butyl lithium or sec-butyl lithium in a solvent such as ether, tetrahydrofuran, dimethylformamide and the resultant anion can react directly with a compound of formula (IV) wherein R3 and A are as defined above and below to afford the compound of the aforementioned formula (I) wherein R4 represents a hydrogen atom.

Compounds of formula (III) and (IV) are commercially available or may be synthesized according to well-known methods to one skilled in the art.

Compounds of formula (IV) wherein A represents a suitable electrophilic group; A is represented as follows, wherein R represents a halogen atom, a hydrogen atom, alkyl group; alkoxy group, perhalogenated alkyl group, and X represents a halogen atoms, a mesylate or a tosylate group:

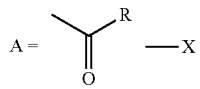

Alternatively, compounds of formula (I) wherein R1, R2, R3, X and m are the same as already described, R4 represents an hydrogen, may be prepared according to the method defined in scheme 2, starting from compound of formula (II). The conditions which may be used are given in the chemical examples.

Scheme 2

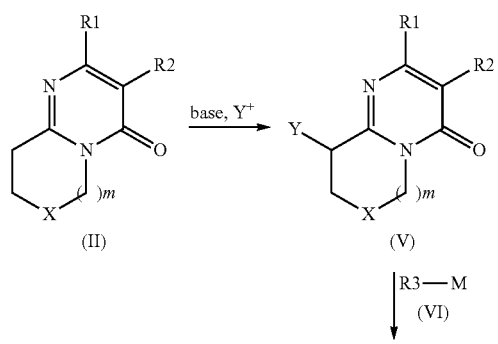

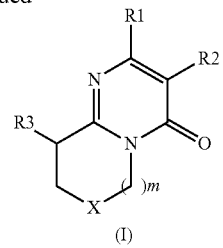

(In the above scheme, the definition of R1, R2, R3, X and m are the same as already described, R4 represents an hydrogen, Y represents an halogen and M represents a metal group which allows the preparation of the pyrimidone derivative represented by the above formula (I)).

According to this method, the pyrimidone derivative represented by the above formula (II), wherein R1, R2, X and m are as defined for compound of formula (I), can be deprotonated with strong base such as sodium hydride, lithium bis(trimethylsilyl)amide, lithium diisopropyl amide, n-butyl lithium, tert-butyl lithium or sec-butyl lithium in a solvent such as ether, tetrahydrofuran, dimethylformamide and the resultant anion can react with a suitable electrophile like N-bromosuccinimide, N-iodosuccinimide, bromine or iodine to provide compound of formula (V). The resultant compound (V) can react with a suitable nucleophile of formula (VI) wherein R3 is as defined for compound of formula (I) and M represents a metal like magnesium, copper, lithium or zinc in a solvent such as tetrahydrofuran, to afford the compound of the aforementioned formula (I).

Compound of formula (II) may be prepared according to the method defined in scheme 3.

Scheme 3

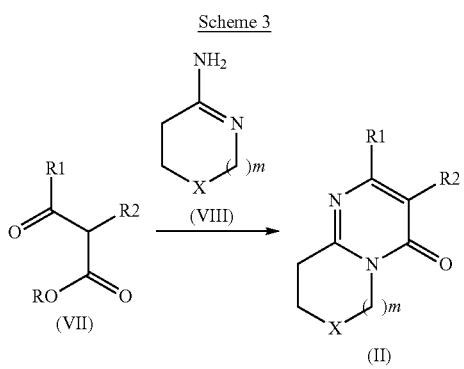

(In the above scheme, the definition of R1, R2, X and m are the same as already described and R represents an alkyl group such as for example methyl or ethyl).

According to this method, the 3-ketoester of formula (VII), wherein R1 and R2 are as defined for compound of formula (I), R is an alkyl group such as for example methyl or ethyl is allowed to react with a compound of formula (VIII) wherein X and m are as defined for compound of formula (I). The reaction may be carried out in the presence of a base such as potassium carbonate, sodium methoxide in an alcoholic solvent such as methanol, ethanol or an inert solvent such as toluene and the like or without, at a suitable temperature ranging from 25° to 140° C. under ordinary air to obtain the compound of the aforementioned formula (II).

Compound of formula (VII) is commercially available or may be synthesized according to well-known methods to one skilled in the art.

For example compounds of formula (VII), wherein R1 represents a pyridine ring or a pyrimidine ring, optionally substituted by a $C_{1-6}$ alkyl group, a $C_{1-6}$ alkoxy group or a halogen atom, can be prepared by reacting respectively an isonicotinic acid or a pyrimidine-carboxylic acid, optionally substituted by a $C_{1-6}$ alkyl group, $C_{1-6}$ alkoxy group or a halogen, with the corresponding malonic acid monoester. The reaction can be carried out using methods well known to one skilled in the art, such as for example in presence of a coupling agent such as 1,1'-carbonylbis-1H-imidazole in a solvent such as tetrahydrofuran at a temperature ranging from 20 to 70° C.

In addition, compounds of formula (VII) wherein R2 represents a fluorine atom may be obtained by analogy to the method described in Tetrahedron Letters, Vol. 30, No. 45, pp 6113-6116, 1989.

In addition, compounds of formula (VII) wherein R2 represents a hydrogen atom may be obtained by analogy to the method described in patent DE 2705582.

As a further object, the present invention concerns also the compounds of formula (II) as intermediates of compounds of formula (I).

Compound of formula (VIII) wherein X represents a nitrogen atom, m represents 2, may be synthesized according to the methods described in WO97/16430 and in Tetrahedron Letters, Vol. 32, No 22, pp 2469-2470, 1991.

Compound of formula (VIII) wherein X represents a carbon atom with m represents 1 or 2 may be synthesized according to the methods described in WO96/14844 and in Journal of Medicinal Chemistry (1998), 41(9), 1361-1366.

In the above reactions protection or deprotection of a functional group may sometimes be necessary. A suitable protecting group Pg can be chosen depending on the type of the functional group, and a method described in the literature may be applied. Examples of protecting groups, of protection and deprotection methods are given for example in Greene's Protective Groups in Organic Synthesis, Greene et al., 4th Ed. (John Wiley & Sons, Inc., New York) 2007.

The compounds of the present invention have inhibitory activity against GSK3β. Accordingly, the compounds of the present invention are useful as an active ingredient for the preparation of a medicament, which enables preventive and/or therapeutic treatment of a disease caused by abnormal GSK3β activity and more particularly of neurodegenerative diseases such as Alzheimer's disease. In addition, the compounds of the present invention are also useful as an active ingredient for the preparation of a medicament for preventive and/or therapeutic treatment of neurodegenerative diseases such as Parkinson's disease, tauopathies (e.g. Fronto temporal dementia, corticobasal degeneration, Pick's disease, progressive supranuclear palsy), Wilson's disease, Huntington's disease, Prion disease and other dementia including vascular dementia; acute stroke and others traumatic injuries; cerebrovascular accidents (e.g. age related macular degeneration); brain and spinal cord trauma; amyotrophic lateral sclerosis, peripheral neuropathies; retinopathies and glaucoma; and other diseases such as non-insulin dependent diabetes (such as diabetes type II) and obesity; malaria, manic depressive illness; schizophrenia; alopecia; cancers such as colorectal, prostate breast cancer, non-small cell lung carcinoma, thyroid cancer, T or B-cell leukemia, several virus-induced tumours and in bone related pathologies; parenchymal renal diseases or muscle atrophy. The medicament could also find an application in regenerative medicine. The medicament could also find an application in the treatment or prevention of *Pemphigus vulgaris*. The medicament could also find an application in the treatment of neutropenia induced by cancer chemotherapy. The medicament could also find an application for therapeutic treatment of a disease characterized by cognitive and memory deficits such as in Alzheimer's disease, Parkinson disease, age associated memory impairment, mild cognitive impairment, brain trauma, schizophrenia and other conditions in which such deficits are observed.

The present invention further relates to a method for treating neurodegenerative diseases caused by abnormal activity of GSK3β and of the aforementioned diseases which comprises administering to a mammalian organism in need thereof an effective amount of a compound of the formula (I).

As the active ingredient of the medicament of the present invention, a substance may be used which is selected from the group consisting of the compound represented by the aforementioned formula (I) and pharmacologically acceptable salts thereof, and solvates thereof and hydrates thereof. The substance, per se, may be administered as the medicament of the present invention; however, it is desirable to administer the medicament in a form of a pharmaceutical composition which comprises the aforementioned substance as an active ingredient and one or more pharmaceutical additives. As the active ingredient of the medicament of the present invention, two or more of the aforementioned substances may be used in combination. The above pharmaceutical composition may be supplemented with an active ingredient of another medicament for the treatment of the above mentioned diseases. The type of pharmaceutical composition is not particularly limited, and the composition may be provided as any formulation for oral or parenteral administration. For example, the pharmaceutical composition may be formulated, for example, in the form of pharmaceutical compositions for oral administration such as granules, fine granules, powders, hard capsules, soft capsules, syrups, emulsions, suspensions, solutions and the like, or in the form of pharmaceutical compositions for parenteral administrations such as injections for intravenous, intramuscular, or subcutaneous administration, drip infusions, transdermal preparations, transmucosal preparations, nasal drops, inhalants, suppositories and the like. Injections or drip infusions may be prepared as powdery preparations such as in the form of lyophilized preparations, and may be used by dissolving just before use in an appropriate aqueous medium such as physiological saline. Sustained-release preparations such as those coated with a polymer may be directly administered intracerebrally.

Types of pharmaceutical additives used for the manufacture of the pharmaceutical composition, content ratios of the pharmaceutical additives relative to the active ingredient, and methods for preparing the pharmaceutical composition may be appropriately chosen by those skilled in the art. Inorganic or organic substances or solid or liquid substances may be used as pharmaceutical additives. Generally, the pharmaceutical additives may be incorporated in a ratio ranging from 1% by weight to 90% by weight based on the weight of an active ingredient.

Examples of excipients used for the preparation of solid pharmaceutical compositions include, for example, lactose, sucrose, starch, talc, cellulose, dextrin, kaolin, calcium carbonate and the like. For the preparation of liquid compositions for oral administration, a conventional inert diluent such as water or a vegetable oil may be used. The liquid composition may contain, in addition to the inert diluent, auxiliaries such as moistening agents, suspension aids, sweeteners, aromatics, colorants, and preservatives. The liquid composition may be filled in capsules made of an absorbable material such as gelatin. Examples of solvents or suspension mediums used for the preparation of compositions for parenteral administration, e.g. injections, suppositories, include water, propylene glycol, polyethylene glycol, benzyl alcohol, ethyl oleate, lecithin and the like. Examples of base materials used for suppositories include, for example, cacao butter, emulsified cacao butter, lauric lipid, witepsol.

The dose and frequency of administration of the medicament of the present invention are not particularly limited, and they may be appropriately chosen depending on conditions such as a purpose of preventive and/or therapeutic treatment, a type of a disease, the body weight or age of a patient, severity of a disease and the like. Generally, a daily dose for oral administration to an adult may be 0.01 to 1,000 mg (the weight of an active ingredient), and the dose may be administered once a day or several times a day as divided portions, or once in several days. When the medicament is used as an injection, administrations may preferably be performed continuously or intermittently in a daily dose of 0.001 to 100 mg (the weight of an active ingredient) to an adult.

CHEMICAL EXAMPLES

Example 1

Compound No. 1 of Table 2

(+/−) 10-Methyl-2-pyrimidin-4-yl-7,8,9,10-tetrahydro-6H-pyrimido[1,2-α]azepin-4-one 1.1 2-Pyrimidin-4-yl-7,8,9,10-tetrahydro-6H-pyrimido[1,2-α]azepin-4-one To a suspension of 77.9 g (524.1 mmol) of 2H-azepin-7-amine, 3,4,5,6-tetrahydro, monohydrochloride (synthesis as described in WO96/14844 or in Journal of Medicinal Chemistry (1998), 41(9), 1361-1366) in 390 mL of ethanol was added 72.4 g (524.1 mmol) of potassium carbonate. The reaction mixture was stirred at room temperature for 10 min, 101.7 g (524.1 mmol) of ethyl 3-(4-pyrimidinyl)-3-oxopropionate was added and the resulting mixture was stirred under reflux for 16 h. The cooled solution was evaporated to remove solvent. The mixture was dissolved in dichloromethane, washed with a saturated aqueous solution of sodium chloride, dried over sodium sulfate and evaporated to dryness. The residue was filtrate through a pad of silica, rinsing with dichloromethane and then ethyl acetate. After evaporation, the resulting solid was triturated in diethyl ether, filtrated to afford 36.4 g (28%) of the desired compound as a white-brown powder.

Mp: 148-150° C.
RMN $^1$H (DMSO-d$^6$; 400 MHz)
δ (ppm): 9.32 (s, 1H), 9.01 (d, 1H), 8.24 (d, 1H), 7.21 (s, 1H), 4.32 (m, 2H), 3.11 (m, 2H), 1.66-1.83 (m, 6H).

1.2 (+/−)-10-Methyl-2-pyrimidin-4-yl-7,8,9,10-tetrahydro-6H-pyrimido[1,2-α]azepin-4-one To a solution of 10.00 g (41.27 mmol) of 2-pyrimidin-4-yl-7,8,9,10-tetrahydro-6H-pyrimido[1,2-α]azepin-4-one in dry tetrahydrofuran (200 mL) under argon at −78° C. was added 82.5 mL (82.5 mmol) of lithium bis(trimethylsilyl) amide (1M in tetrahydrofuran). The solution was stirred at −78° C. for 10 min and 25.7 mL of methyl iodide (412.7 mmol) was added. The reaction was stirred at −78° C. for 1 h and then at 0° C. for 2 h. The mixture was quenched with the addition of a saturated solution of ammonium chloride and extracted with ethyl acetate. The organic phase was dried over sodium sulfate and concentrated. The residue was purified by flash chromatography (dichloromethane with 1% of methanol) to afford 11.0 g of a white solid (40%).

Mp: 182-184° C.
RMN $^1$H (DMSO-d$^6$; 400 MHz)
δ (ppm): 9.31 (s, 1H), 9.03 (d, 1H), 8.30 (d, 1H), 7.22 (s, 1H), 5.02 (m, 1H), 3.70 (m, 1H), 3.40 (m, 1H), 2.00 (m, 1H), 1.78-1.90 (m, 3H), 1.30-1.48 (m, 5H).

Example 2

Compound No. 2 of Table 2

(+/−) 10-Methyl-2-pyridin-4-yl-7,8,9,10-tetrahydro-6H-pyrimido[1,2-α]azepin-4-one 2.1 2-Pyridin-4-yl-7,8,9,10-tetrahydro-6H-pyrimido[1,2-α]azepin-4-one By analogy with the method described in example 1 (step 1.1), using ethyl 3-(pyridin-4-yl)-3-oxopropionate in place of ethyl 3-(4-pyrimidinyl)-3-oxopropionate, 20.0 g of the compound (54%) was obtained as a white powder.

Mp: 148-150° C.
RMN $^1$H (DMSO-d$^6$; 400 MHz)
δ (ppm): 8.79 (d, 2H), 8.01 (d, 2H), 7.08 (s, 1H), 4.31 (m, 2H), 3.11 (m, 2H), 1.80 (m, 4H), 1.78 (m, 2H).

2.2 (+/−) 10-Methyl-2-pyridin-4-yl-7,8,9,10-tetrahydro-6H-pyrimido[1,2-α]azepin-4-one By analogy with the method described in example 1 (step 1.2), using 2-pyridin-4-yl-7,8,9,10-tetrahydro-6H-pyrimido[1,2-α]azepin-4-one in place of 2-pyrimidin-4-yl-7,8,9,10-tetrahydro-6H-pyrimido[1,2-α]azepin-4-one, 1.13 g of the compound (21%) was obtained as a orange powder.

Mp: 137-139° C.
RMN $^1$H (DMSO-d$^6$; 400 MHz)
δ (ppm): 8.72 (d, 2H), 8.08 (d, 2H), 7.09 (s, 1H), 5.01 (m, 1H), 3.68 (m, 1H), 3.37 (m, 2H), 1.98 (m, 1H), 1.83 (m, 2H), 1.49-1.25 (m, 5H).

Example 3

Compound No. 3 of Table 2

(+/−) 10-Ethyl-2-pyrimidin-4-yl-7,8,9,10-tetrahydro-6H-pyrimido[1,2-α]azepin-4-one By analogy with the method described in example 1 (step 1.2) using ethyl iodide instead of methyl iodide, 0.46 g of the compound (21%) was obtained as a white powder.

Mp: 128-130° C.
RMN $^1$H (DMSO-d$^6$; 400 MHz)
δ (ppm): 9.32 (s, 1H), 9.08 (d, 1H), 8.27 (d, 1H), 7.22 (s, 1H), 4.98 (m, 1H), 3.78 (m, 1H), 3.12 (m, 1H), 2.15 (m, 1H), 1.95 (m, 2H), 1.80 (m, 2H), 1.60 (m, 1H), 1.35 (m, 2H), 1.08 (t, 3H).

Example 4

Compound No. 8 of Table 2

(+/−)-10-[(4-Fluoro-2-methoxy-phenyl)-hydroxy-methyl]-2-pyrimidin-4-yl-7,8,9,10-tetrahydro-6H-pyrimido[1,2-α]azepin-4-one To a solution of 0.500 g (2.06 mmol) of 2-pyrimidin-4-yl-7,8,9,10-tetrahydro-6H-pyrimido[1,2-α]azepin-4-one (step 4.1) in dry tetrahydrofuran (20 mL) under argon at −40° C. was added 2.48 mL (2.48 mmol) of lithium bis(trimethylsilyl) amide (1M in tetrahydrofuran). The solution was stirred at −40° C. for 10 min and 0.636 g of 4-fluoro-2-methoxy-benzaldehyde (4.13 mmol) diluted in 5 ml of dry tetrahydrofuran was added. The reaction was allowed to increase to room temperature for 2 h. The mixture was quenched with the addition of a saturated solution of ammonium chloride and extracted with dichloromethane. The organic phase was dried over sodium sulfate and concentrated. The residue was purified by flash chromatography (dichloromethane with 2% of methanol and 0.2% of ammonia) to afford 0.505 g of a white solid (62%).

Mp: 235-237° C.

RMN $^1$H (DMSO-d$^6$; 400 MHz)

δ (ppm): 9.30 (s, 1H), 9.05 (d, 1H), 8.15 (d, 1H), 7.52 (m, 1H), 7.18 (s, 1H), 6.88 (d, 1H), 6.72 (m, 1H), 5.58 (m, 1H), 5.28 (m, 1H), 4.88 (m, 1H), 3.92 (m, 1H), 3.85 (s, 3H), 3.60 (m, 1H), 2.12 (m, 1H), 1.92 (m, 2H), 1.58 (m, 2H), 1.42 (m, 1H).

Example 5

Compound No. 10 of Table 2

(+/−)-10-[Fluoro-(4-fluoro-2-methoxy-phenyl)-methyl]-2-pyrimidin-4-yl-7,8,9,10-tetrahydro-6H-pyrimido[1,2-α]azepin-4-one To a solution of 0.290 g (0.73 mmol) of (+/−)-10-[(4-fluoro-2-methoxy-phenyl)-hydroxy-methyl]-2-pyrimidin-4-yl-7,8,9,10-tetrahydro-6H-pyrimido[1,2-α]azepin-4-one (example 4) in dichloromethane (14 mL) under argon at −78° C. was added 0.294 g of diethylaminosulfur trifluoride (1.83 mmol) diluted in 5 ml of dichloromethane. The reaction was allowed to increase to room temperature. The reaction was stirred at room temperature for 2 h; the mixture was quenched at 0° C. with the addition of methanol and stirred overnight. A saturated solution of ammonium chloride was added and the mixture was extracted with dichloromethane. The organic phase was washed with a saturated solution of sodium chloride and dried over sodium sulfate and concentrated. The residue was purified by flash chromatography (dichloromethane with 2% of methanol and 0.2% of ammonia) to afford 0.072 g (25%) of a white solid as an isomer mixture (95/5).

Mp: 228-230° C.

RMN $^1$H (DMSO-d$^6$; 400 MHz)

δ (ppm): 9.28 (s, 1H), 9.08 (d, 1H), 8.00 (d, 1H), 7.68 (m, 1H), 7.18 (s, 1H), 6.98 (d, 1H), 6.78 (m, 1H), 6.35 (dd, 1H), 4.98 (m, 1H), 4.20 (m, 1H), 3.98 (s, 3H), 3.97 (m, 1H), 2.35 (m, 1H), 2.05-1.80 (m, 3H), 1.68 (m, 1H), 1.42 (m, 1H).

Example 6

Compound No. 12 of Table 2

(+/−)-10-[2-(2-Methoxy-phenyl)-ethyl]-2-pyrimidin-4-yl-7,8,9,10-tetrahydro-6H-pyrimido[1,2-α]azepin-4-one To a solution of 0.500 g (2.06 mmol) of 2-pyrimidin-4-yl-7,8,9,10-tetrahydro-6H-pyrimido[1,2-α]azepin-4-one in dry tetrahydrofuran (20 mL) under argon at −30° C. was added 3.10 mL (3.10 mmol) of lithium bis(trimethylsilyl)amide (1M in tetrahydrofuran). The solution was stirred at room temperature for 10 min and 1.31 mL of 1-(2-bromo-ethyl)-2-methoxy-benzene (8.25 mmol) was added. The reaction was stirred at 70° C. for 6 hours. The mixture was quenched with the addition of a saturated solution of ammonium chloride and extracted with dichloromethane. The organic phase was dried over sodium sulfate and concentrated. The residue was purified by flash chromatography (dichloromethane with 3% of methanol and 0.3% of ammonia) to afford 0.087 g of a solid (11%).

Mp: 155-157° C.

RMN $^1$H (DMSO-d$^6$; 400 MHz)

δ (ppm): 9.30 (s, 1H), 9.08 (d, 1H), 8.28 (d, 1H), 7.25 (s, 1H), 7.18 (m, 1H), 6.96 (m, 1H), 6.90 (m, 1H), 4.98 (m, 1H), 3.78 (s, 3H), 3.69 (m, 1H), 3.20 (m, 1H), 2.78 (m, 2H), 1.95 (m, 2H), 1.95 (m, 1H), 1.80 (m, 3H), 1.41 (m, 3H).

Example 7

Compound No. 26 of Table 2

(+)-10-(4-Fluoro-benzyl)-2-pyrimidin-4-yl-7,8,9,10-tetrahydro-6H-pyrimido[1,2-α]azepin-4-one 0.090 g of (+/−)-10-(4-fluoro-benzyl)-2-pyrimidin-4-yl-7,8,9,10-tetrahydro-6H-pyrimido[1,2-α]azepin-4-one was separated by chiral preparative HPLC (CHIRALPAK AD 20 μm; 6×35 cm) eluting with heptane/ethanol (50/50) to give 0.044 g of pure product obtained in the form of free base.

Mp: 174-175° C. $[α]_D^{20}$=+70.3° (c=1.929 mg/0.5 mL MeOH).

RMN $^1$H (DMSO; 400 MHz)

δ (ppm): 9.32 (s, 1H), 9.02 (d, 1H), 8.31 (d, 1H), 7.45 (m, 2H), 7.22 (s, 1H), 7.11 (m, 2H), 5.00 (m, 1H), 3.80 (m, 1H), 3.65 (m, 1H), 3.47 (m, 1H), 2.90 (m, 1H), 1.97 (m, 1H), 1.80 (m, 2H), 1.61 (m, 1H), 1.38 (m, 2H).

Example 8

Compound No. 27 of Table 2

(−)-10-(4-Fluoro-benzyl)-2-pyrimidin-4-yl-7,8,9,10-tetrahydro-6H-pyrimido[1,2-α]azepin-4-one 0.090 g of (+/−)-10-(4-fluoro-benzyl)-2-pyrimidin-4-yl-7,8,9,10-tetrahydro-6H-pyrimido[1,2-α]azepin-4-one was separated by chiral preparative HPLC (CHIRALPAK AD 20 μm; 6×35 cm) eluting with heptane/ethanol (50/50) to give 0.043 g of pure product obtained in the form of free base.

Mp: 174-175° C. $[α]_D^2$=−63° (c=2.390 mg/1 mL MeOH).

RMN $^1$H (DMSO; 400 MHz)

δ (ppm): 9.32 (s, 1H), 9.02 (d, 1H), 8.31 (d, 1H), 7.45 (m, 2H), 7.22 (s, 1H), 7.11 (m, 2H), 5.00 (m, 1H), 3.80 (m, 1H), 3.65 (m, 1H), 3.47 (m, 1H), 2.90 (m, 1H), 1.97 (m, 1H), 1.80 (m, 2H), 1.61 (m, 1H), 1.38 (m, 2H).

Example 9

Compound No. 20 of Table 2

(+/−)-10-Cyclopropyl-2-pyrimidin-4-yl-7,8,9,10-tetrahydro-6H-pyrimido[1,2-α]azepin-4-one 9.1 (+/−)-10-Bromo-2-pyrimidin-4-yl-7,8,9,10-tetrahydro-6H-pyrimido[1,2-α]azepin-4-one To a solution of 1.00 g (4.13 mmol) of 2-pyrimidin-4-yl-7,8,9,10-tetrahydro-6H-pyrimido[1,2-α]azepin-4-one (step 4.1 of example 4) in 35 mL of dry tetrahydrofuran at −50° C., was added 8.25 mL (8.25 mmol) of lithium bis(trimethylsilyl) amide (1M in tetrahydrofuran). The resulting mixture was stirred at −50° C. for 10 min. 0.808 g (4.54 mmol) of N-bromo-succinimide dissolved in 5 mL of tetrahydrofuran was added at −50° C. the resulting mixture was stirred for 1 hours. The mixture was dissolved in a saturated solution of ammonium chloride and ethyl acetate. The organic phases were washed with a saturated aqueous solution of sodium chloride, dried over sodium sulfate and evaporated to dryness. The residue was purified by flash chromatography (cyclohexane/ethyl acetate in proportions of 90/10) to afford 0.410 g (31%) of a white solid.

Mp: 117-119° C.

RMN $^1$H (DMSO; 400 MHz)

δ (ppm): 9.45 (s, 1H), 9.08 (d, 1H), 8.25 (d, 1H), 7.32 (s, 1H), 5.71 (m, 1H), 5.01 (m, 1H), 3.98 (m, 1H), 2.23 (m, 2H), 1.98-1.87 (m, 3H), 1.55 (m, 1H).

9.2 (+/−)-10-Cyclopropyl-2-pyrimidin-4-yl-7,8,9,10-tetrahydro-6H-pyrimido[1,2-α]azepin-4-one To a solution of 1.33 g (6.48 mmol) of CuBr.DMS in 25 mL of dry tetrahydrofuran at −78° C., was slowly added 12.45 mL (6.23 mmol) of cyclopropyl magnesium bromide (0.5 M in tetrahydrofuran). The resulting mixture was stirred at room temperature for 30 min. 0.800 g (2.49 mmol) of (+/−)-10-bromo-2-pyrimidin-4-yl-7,8,9,10-tetrahydro-6H-pyrimido [1,2-α]azepin-4-one dissolved in 10 mL of dry tetrahydrofuran was added at −78° C. and the resulting mixture was stirred for 1.5 hours and allowed to warm to room temperature. The mixture was dissolved in a saturated solution of ammonium chloride and ethyl acetate. The organic phases were washed with a saturated aqueous solution of sodium chloride, dried over sodium sulfate and evaporated to dryness. The residue was purified by flash chromatography (dichloromethane/methanol/ammoniac in proportions of 99/1/0.1) to afford 0.230 g (33%) of a white solid.

Mp: 139-140° C.

RMN $^1$H (DMSO; 400 MHz)

9.30 (s, 1H), 9.00 (d, 1H), 8.30 (d, 1H), 7.20 (s, 1H), 4.89 (m, 1H), 3.55 (m, 1H), 2.45 (m, 1H), 2.02 (m, 1H), 1.92-1.28 (m, 6H), 0.61 (m, 2H), 0.25 (m, 2H).

Example 10

Compound No. 1 of Table 3

(+/−)-9-Ethyl-4-oxo-2-pyrimidin-4-yl-5,6,8,9-tetrahydro-4H-1,4-a,7-triaza-benzocycloheptene-7-carboxylic acid ethyl ester 10.1 4-oxo-2-pyrimidin-4-yl-5,6,8,9-tetrahydro-4H-1,4-a,7-triaza-benzocycloheptene-7-carboxylic acid ethyl ester To a suspension of 13.4 g (60.45 mmol) of 5-amino-2,3,6,7-tetrahydro-[1,4]diazepine-1-carboxylic acid ethyl ester monohydrochloride (synthesis as described in WO9716430) in 50 mL of ethanol was added 10.29 g (74.50 mmol) of potassium carbonate. The reaction mixture was stirred at room temperature for 10 min, 14.47 g (74.50 mmol) of ethyl 3-(4-pyrimidinyl)-3-oxopropionate was added and the resulting mixture was stirred under reflux for 2.5 hours. The cooled solution was evaporated to remove solvent. The mixture was dissolved with water and diethyl ether. After stirring, the resulting solid was filtered, washed with water and diethyl ether to afford 8.80 g (46%) of the desired compound as a powder.

Mp: 144-146° C.

RMN $^1$H (DMSO-d$^6$; 400 MHz)

δ (ppm): 9.34 (s, 1H), 9.06 (d, 1H), 8.28 (d, 1H), 7.29 (s, 1H), 4.42 (m, 2H), 4.10 (m, 2H), 3.72 (m, 4H), 3.29 (m, 2H), 1.20 (t, 3H).

10.2 (+/−)-9-Ethyl-4-oxo-2-pyrimidin-4-yl-5,6,8,9-tetrahydro-4H-1,4-a,7-triaza-benzocycloheptene-7-carboxylic acid ethyl ester To a solution of 10.00 g (41.27 mmol) of 4-oxo-2-pyrimidin-4-yl-5,6,8,9-tetrahydro-4H-1,4-a,7-triaza-benzocycloheptene-7-carboxylic acid ethyl ester in dry tetrahydrofuran (8 mL) under argon at −78° C. was added 2.00 mL (2.00 mmol) of lithium bis(trimethylsilyl)amide (1M in tetrahydrofuran). The solution was stirred at −78° C. for 10 min and 1.28 mL of ethyl iodide (15.86 mmol) was added. The reaction was stirred at −78° C. for 1 h and then at 0° C. for 2 h. The mixture was quenched with the addition of a saturated solution of ammonium chloride and extracted with ethyl acetate. The organic phase was dried over sodium sulfate and concentrated. The residue was purified by flash chromatography (dichloromethane with 1% of methanol) to afford 0.100 g of a white solid (18%).

Mp: 160-162° C.

RMN $^1$H (DMSO-d$^6$; 400 MHz)

δ (ppm): 9.32 (s, 1H), 9.08 (d, 1H), 8.28 (d, 1H), 7.30 (s, 1H), 4.88 (m, 1H), 4.05 (m, 3H), 3.91 (m, 2H), 3.41 (m, 1H), 3.30 (m, 2H), 2.12 (m, 1H), 1.68 (m, 1H), 1.18 (t, 3H), 1.08 (t, 3H).

Example 11

Compound No. 2 of Table 3

(+/−)-9-Ethyl-2-pyrimidin-4-yl-6,7,8,9-tetrahydro-5H-1,4-a,7-triaza-benzocyclohepten-4-one hydrobromide (1:1)

To a solution of 0.075 g (0.22 mmol) of (+/−)-9-ethyl-4-oxo-2-pyrimidin-4-yl-5,6,8,9-tetrahydro-4H-1,4-a,7-triaza-benzocycloheptene-7-carboxylic acid ethyl ester (example 10) dissolved in 0.8 mL of glacial acetic acid was added 0.77 mL (4.37 mmol) of hydrobromic acid (33 wt % solution in glacial acetic acid). The resulting mixture was stirred at 90° C. for 4 hours, cooled and evaporated to dryness. Methanol was added to the residue and evaporated. Toluene was added to the residue and evaporated. The crude was triturated with diethyl ether and filtered to afford 0.068 g of the product as a white powder (88%).

Mp: 278-280° C.

RMN $^1$H (DMSO; 400 MHz)

δ (ppm): 9.38 (s, 1H), 9.20 (br s, 1H), 9.10 (d, 1H), 8.28 (d, 1H), 7.32 (s, 1H), 5.18 (m, 1H), 4.10 (m, 1H), 3.67 (m, 1H), 3.48 (m, 2H), 3.18 (m, 2H), 2.26 (m, 1H), 1.69 (m, 1H), 1.10 (t, 3H).

Example 12

Compound No. 4 of Table 1

(+/−)-9-(5-Bromo-2-methoxy-benzyl)-2-pyrimidin-4-yl-6,7,8,9-tetrahydro-pyrido[1,2-α]pyrimidin-4-one

12.1 2-Pyrimidin-4-yl-6,7,8,9-tetrahydro-pyrido[1,2-α]pyrimidin-4-one

To a suspension of 25.0 g (185.72 mmol) of 3,4,5,6-tetrahydro-pyridin-2-ylamine monohydrochloride in 138 mL of ethanol was added 25.67 g (185.72 mmol) of potassium carbonate. The reaction mixture was stirred at room temperature for 10 min, 36.06 g (185.72 mmol) of ethyl 3-(4-pyrimidinyl)-3-oxopropionate was added and the resulting mixture was stirred under reflux for 16 h. The cooled solution was evaporated to remove solvent. The mixture was dissolved in ethylacetate, washed with a saturated aqueous solution of sodium chloride, dried over sodium sulfate and evaporated to dryness. The resulting solid was triturated in diethyl ether, filtrated to afford 9.23 g (22%) of the desired compound as a white-brown powder.
Mp: 177-179° C.
RMN $^1$H (DMSO-d$^6$; 400 MHz)
δ (ppm): 9.32 (s, 1H), 9.05 (d, 1H), 8.25 (d, 1H), 7.22 (s, 1H), 3.89 (m, 2H), 3.00 (m, 2H), 1.98-1.88 (m, 4H).

12.2 (+/−)-9-(5-Bromo-2-methoxy-benzyl)-2-pyrimidin-4-yl-6,7,8,9-tetrahydropyrido[1,2-α]pyrimidin-4-one By analogy with the method described in example 10 (step 10.2), using 4-Bromo-2-bromomethyl-1-methoxy-benzene in place of ethyl iodide, 0.394 g of the compound (53%) was obtained as a white powder.
Mp: 178-180° C.
RMN $^1$H (DMSO-d$^6$; 400 MHz)
δ (ppm): 9.40 (s, 1H), 9.10 (d, 1H), 8.10 (d, 1H), 7.40 (m, 2H), 7.20 (s, 1H), 7.00 (d, 1H); 4.05 (m, 1H), 3.80 (m, 4H); 3.50 (m, 1H); 3.30 (d, 1H); 2.90 (ddd, 1H); 1.90 (m, 3H); 1.60 (m, 1H).

A list of chemical structures and physical data for compounds of the aforementioned formula (I), illustrating the present invention, is given in table 1 to 3. The compounds have been prepared according to the methods of the examples.

In the table 1, m represents 1, X represents CH$_2$, Me represents a methyl group, (Rot.) indicates the levorotatory or dextrorotatory properties of the enantiomeric compound, (dec.) indicates the decomposition of the compound. Table 1A provides analytic data for the compounds of table 1.

TABLE 1

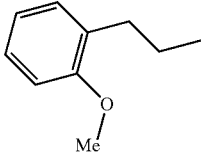
(I)

| No. | Rot | R3 | R1 | R4 | R2 | salt |
|---|---|---|---|---|---|---|
| 1 | (+/−) | 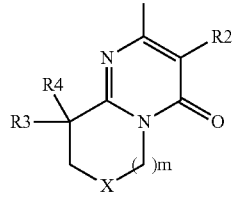 | 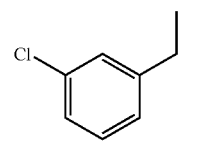 | H | H | Hydrochloride (1:1) |
| 2 | (+/−) | 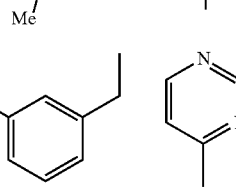 | 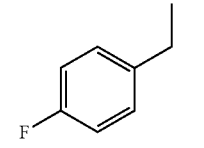 | H | H | Free base |
| 3 | (+/−) | 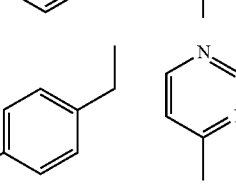 | 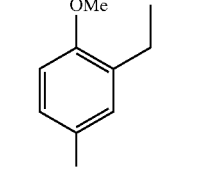 | H | H | Free base |
| 4 | (+/−) | 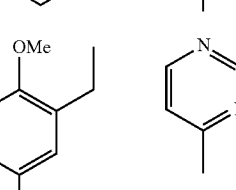 |  | H | H | Free base |

TABLE 1A

| N° | Mp ° C. | | NMR | |
|---|---|---|---|---|
| 1 | 240-242 | 300 MHz | D$_2$O | δ (ppm): 9.00 (d, 2H); 8.50 (d, 2H); 7.30 (d, 1H); 7.20 (m, 1H), 7.10 (s, 1H); 6.90 (m, 2H); 4.15 (m, 1H), 4.00 (m, 1H); 3.80 (s, 3H); 3.20 (m, 1H); 2.90 (m, 2H); 2.50-2.30 (m, 2H); 2.20 (m, 2H); 2.00 (m, 2H). |
| 2 | 181-183 | 400 MHz | DMSO d6 | δ (ppm): 9.35 (s, 1H); 9.00 (d, 1H); 8.20 (d, 1H); 7.50-7.30 (m, 4H); 7.20 (s, 1H); 4.10 (m, 1H), 3.85 (m, 1H); 3.65 (m, 1H); 3.30 (m, 1H); 2.90 (m, 1H); 1.90 (m, 3H); 1.60 (m, 1H). |
| 3 | 202-203 | 400 MHz | DMSO d6 | δ (ppm): 9.35 (s, 1H); 9.00 (d, 1H); 8.30 (d, 1H); 7.30 (m, 2H); 7.20 (s, 1H); 7.15 (m, 2H); 4.00 (m, 1H), 3.85 (m, 1H); 3.60 (m, 1H); 3.30 (m, 1H); 2.90 (m, 1H); 1.90 (m, 3H); 1.60 (m, 1H). |
| 4 | 178-180 | 400 MHz | DMSO d6 | δ (ppm): 9.40 (s, 1H); 9.10 (d, 1H); 8.10 (d, 1H); 7.40 (m, 2H); 7.20 (s, 1H); 7.00 (d, 1H); 4.05 (m, 1H), 3.80 (m, 4H); 3.50 (m, 1H); 3.30 (d, 1H); 2.90 (ddd, 1H); 1.90 (m, 3H); 1.60 (m, 1H). |

A list of chemical structures and physical data for compounds of the aforementioned formula (I), illustrating the present invention, is given in table 2. The compounds have been prepared according to the methods of the examples.

In the table 2, m represents 2, X represents $CH_2$, Me represents a methyl group, (Rot.) indicates the levorotatory or dextrorotatory properties of the enantiomeric compound, (dec.) indicates the decomposition of the compound. Table 2A provides analytic data for the compounds of table 2.

TABLE 2

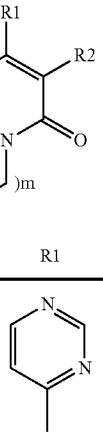

(I)

| No. | Rot | R3 | R1 | R4 | R2 | salt |
|---|---|---|---|---|---|---|
| 1 | (+/−) | Me | 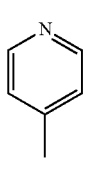 | H | H | Free base |
| 2 | (+/−) | Me |  | H | H | Free base |
| 3 | (+/−) | 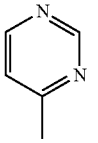 |  | H | H | Free base |
| 4 | (+/−) | 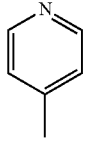 | 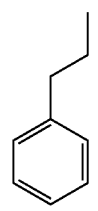 | H | H | Free base |
| 5 | (+/−) | 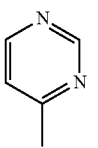 | 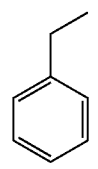 | H | H | Free base |
| 6 | (+/−) | 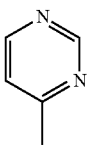 | 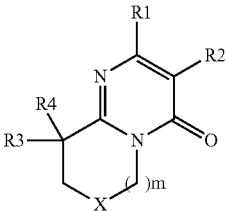 | H | H | Free base |

TABLE 2-continued

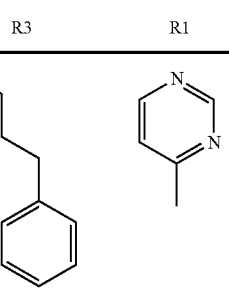

(I)

| No. | Rot | R3 | R1 | R4 | R2 | salt |
|---|---|---|---|---|---|---|
| 7 | (+/−) | 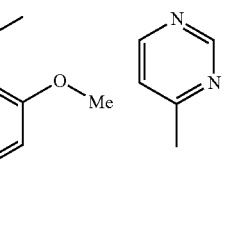 | 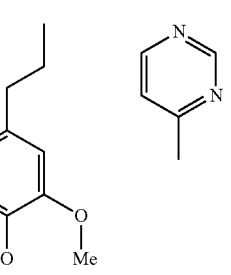 | H | H | Free base |
| 8 | (+/−) | 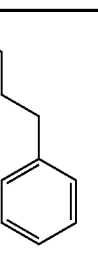 | 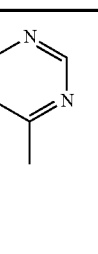 | H | H | Free base |
| 9 | (+/−) | 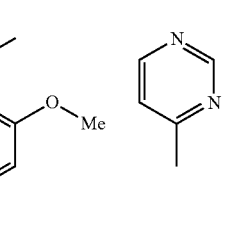 | 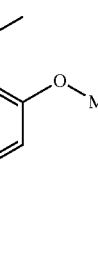 | H | H | Free base |
| 10 | (+/−) | 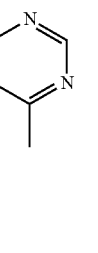 | 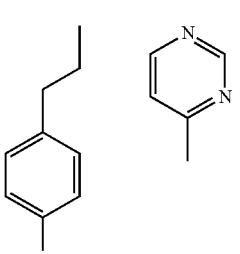 | H | H | Free base |
| 11 | (+/−) | 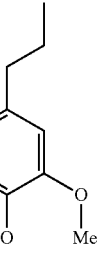 | 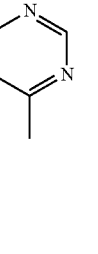 | H | H | Free base |

TABLE 2-continued (I)

| No. | Rot | R3 | R1 | R4 | R2 | salt |
|---|---|---|---|---|---|---|
| 12 | (+/−) | 3-(2-methoxyphenyl)propyl | 4-methylpyrimidin-2-yl | H | H | Free base |
| 13 | (+/−) | 2-methyl-2-phenylpropyl (with extra Me) | 4-methylpyrimidin-2-yl | H | H | Free base |
| 14 | (+/−) | sec-butyl (Me-CH(Me)-CH2-) | 4-methylpyrimidin-2-yl | H | H | Free base |
| 15 | (+/−) | 3-(4-fluoro-2-methoxyphenyl)propyl | 4-methylpyrimidin-2-yl | H | H | Free base |
| 16 | (+/−) | 3-(2,4-difluorophenyl)propyl | 4-methylpyrimidin-2-yl | H | H | Free base |
| 17 | (+/−) | 2-hydroxy-3-phenylpropyl | 4-methylpyrimidin-2-yl | H | H | Free base |
| 18 | (+/−) | cyclopentylmethyl | 4-methylpyrimidin-2-yl | H | H | Free base |
| 19 | (+/−) | 2-fluoro-3-phenylpropyl | 4-methylpyrimidin-2-yl | H | H | Free base |
| 20 | (+/−) | cyclopropylmethyl | 4-methylpyrimidin-2-yl | H | H | Free base |
| 21 | (+/−) | 2-hydroxy-2-(trifluoromethyl)-3-(4-methoxyphenyl)propyl | 4-methylpyrimidin-2-yl | H | H | Free base |
| 22 | (+/−) | 2-hydroxypropyl | 4-methylpyrimidin-2-yl | H | H | Free base |
| 23 | (+/−) | 2-fluoropropyl | 4-methylpyrimidin-2-yl | H | H | Free base |

TABLE 2-continued (I)

| No. | Rot | R3 | R1 | R4 | R2 | salt |
|---|---|---|---|---|---|---|
| 24 | (+/−) | 4-fluorobenzyl | 4-pyrimidinyl | H | H | Free base |
| 25 | (+/−) | 2-hydroxy-3-phenylpropyl | 4-pyrimidinyl | Me | H | Free base |
| 26 | (+) | 4-fluorophenethyl | 4-methylpyrimidin-2-yl | H | H | Free base |
| 27 | (−) | 4-fluorophenethyl | 4-methylpyrimidin-2-yl | H | H | Free base |

TABLE 2A

| N° | Mp ° C. | NMR | | |
|---|---|---|---|---|
| 1 | 182-184 | 400 MHz | DMSO d6 | δ (ppm): 9.31 (s, 1H), 9.03 (d, 1H), 8.30 (d, 1H), 7.22 (s, 1H), 5.02 (m, 1H), 3.70 (m, 1H), 3.40 (m, 1H), 2.00 (m, 1H), 1.78-1.90 (m, 3H), 1.30-1.48 (m, 5H). |
| 2 | 137-139 | 400 MHz | DMSO d6 | δ (ppm): 8.72 (d, 2H), 8.08 (d, 2H), 7.09 (s, 1H), 5.01 (m, 1H), 3.68 (m, 1H), 3.37 (m, 2H), 1.98 (m, 1H), 1.83 (m, 2H), 1.49-1.25 (m, 5H). |
| 3 | 128-130 | 400 MHz | DMSO d6 | δ (ppm): 9.32 (s, 1H), 9.08 (d, 1H), 8.27 (d, 1H), 7.22 (s, 1H), 4.98 (m, 1H), 3.78 (m, 1H), 3.12 (m, 1H), 2.15 (m, 1H), 1.95 (m, 2H), 1.80 (m, 2H), 1.60 (m, 1H), 1.35 (m, 2H), 1.08 (t, 3H). |
| 4 | 111-113 | 400 MHz | DMSO d6 | δ (ppm): 8.85 (d, 2H), 8.05 (d, 2H), 7.10 (s, 1H), 5.00 (dd, 1H), 3.68 (ddd, 1H), 3.10 (m, 1H), 2.15 (m, 1H), 1.90 (m, 2H), 1.75 (m, 2H), 1.60 (m, 1H), 1.35 (m, 2H), 1.05 (t, 3H). |
| 5 | 127-129 | 400 MHz | DMSO d6 | δ (ppm): 9.35 (s, 1H), 9.10 (d, 1H), 8.25 (d, 1H), 7.40-7.10 (m, 6H), 5.00 (dd, 1H), 3.68 (ddd, 1H), 3.30 (m, 1H), 2.80 (m, 2H), 2.50 (m, 1H), 2.00 (m, 2H), 1.80 (m, 3H), 1.50-1.30 (m, 2H). |
| 6 | 198-200 | 400 MHz; | DMSO d6 | δ (ppm): 9.35 (s, 1H), 9.10 (d, 1H), 8.35 (d, 1H), 7.40 (d, 2H), 7.30 (m, 2H), 7.25 (s, 1H), 7.20 (m, 1H), 5.00 (dd, 1H), 3.80 (ddd, 1H), 3.65 (m, 1H), 3.50 (m, 1H), 2.90 (m, 1H), 2.00-1.50 (m, 4H), 1.35 (m, 2H). |
| 7 | 134-136 | 400 MHz; | DMSO d6 | δ (ppm): 9.35 (s, 1H), 9.10 (d, 1H), 8.10 (d, 1H), 7.40-7.10 (m, 6H), 5.00 (dd, 1H), 3.68 (ddd, 1H), 3.25 (m, 1H), 2.70 (m, 2H), 2.20 (m, 1H), 1.90 (m, 2H), 1.70 (m, 4H), 1.60 (m, 1H), 1.35 (m, 2H). |
| 8 | 235-237 | 400 MHz; | DMSO d6 | δ (ppm): 9.30 (s, 1H), 9.05 (d, 1H), 8.15 (d, 1H), 7.52 (m, 1H), 7.18 (s, 1H), 6.88 (d, 1H), 6.72 (m, 1H), 5.58 (m, 1H), 5.28 (m, 1H), 4.88 (m, 1H), 3.92 (m, 1H), 3.85 (s, 3H), 3.60 (m, 1H), 2.12 (m, 1H), 1.92 (m, 2H), 1.58 (m, 2H), 1.42 (m, 1H). |
| 9 | 130-132 | 400 MHz; | DMSO d6 | δ (ppm): 9.35 (s, 1H), 9.10 (d, 1H), 8.25 (d, 1H), 7.30 (s, 1H), 6.90 (d, 1H), 6.80 (s, 1H), 6.75 (m, 1H), 5.00 (dd, 1H), 3.68 (m, 1H), 3.80-3.65 (m, 7H), 3.30 (m, 1H), 2.70 (m, 2H), 2.50 (m, 1H), 2.00 (m, 2H), 1.80 (m, 3H), 1.50-1.30 (m, 2H). |

TABLE 2A-continued

| N° | Mp ° C. | NMR | | |
|---|---|---|---|---|
| 10 | 228-230 | 400 MHz; | DMSO d6 | δ (ppm): 9.28 (s, 1H), 9.08 (d, 1H), 8.00 (d, 1H), 7.68 (m, 1H), 7.18 (s, 1H), 6.98 (d, 1H), 6.78 (m, 1H), 6.35 (dd, 1H), 4.98 (m, 1H), 4.20 (m, 1H), 3.98 (s, 3H), 3.97 (m, 1H), 2.35 (m, 1H), 2.05-1.80 (m, 3H), 1.68 (m, 1H), 1.42 (m, 1H). |
| 11 | 140-142 | 400 MHz; | DMSO d6 | δ (ppm): 9.35 (s, 1H), 9.10 (d, 1H), 8.25 (d, 1H), 7.30 (s, 1H), 7.20 (d, 2H), 6.80 (d, 2H), 5.00 (dd, 1H), 3.80 (m, 4H), 3.25 (m, 1H), 2.70 (t, 2H), 2.50 (m, 1H), 2.00 (m, 2H), 1.80 (m, 3H), 1.50-1.30 (m, 2H). |
| 12 | 155-157 | 400 MHz; | DMSO d6 | δ (ppm): 9.30 (s, 1H), 9.08 (d, 1H), 8.28 (d, 1H), 7.25 (s, 1H), 7.18 (m, 1H), 6.96 (m, 1H), 6.90 (m, 1H), 4.98 (m, 1H), 3.78 (s, 3H), 3.69 (m, 1H), 3.20 (m, 1H), 2.78 (m, 2H), 1.95 (m, 2H), 1.95 (m, 1H), 1.80 (m, 3H), 1.41 (m, 3H). |
| 13 | 105-107 | 400 MHz; | DMSO d6 | δ (ppm): 9.35 (s, 1H), 9.10 (d, 1H), 8.25 (d, 1H), 7.40 (m, 2H), 7.30-7.00 (m, 4H), 4.50 (br s, 1H), 3.90 (br s, 1H), 3.10 (br s, 1H), 2.90 (m, 1H), 1.80 (dd, 1H), 1.70-1.30 (m, 12H). |
| 14 | 105-107 | 400 MHz; | DMSO d6 | δ (ppm): 9.32 (s, 1H), 9.08 (d, 1H), 8.27 (d, 1H), 7.22 (s, 1H), 4.90 (m, 1H), 3.85 (m, 1H), 3.30 (m, 1H), 2.15 (m, 1H), 1.95-1.70 (m, 4H), 1.50-1.30 (m, 4H), 0.95 (t, 6H). |
| 15 | 134-136 | 400 MHz; | DMSO d6 | δ (ppm): 9.35 (s, 1H), 9.10 (d, 1H), 8.25 (d, 1H), 7.30 (s, 1H), 7.20 (dd, 1H), 6.90 (d, 1H), 6.75 (dd, 1H), 5.00 (dd, 1H), 3.80 (s, 3H); 3.70 (m, 1H), 3.20 (m, 1H), 2.75 (m, 2H), 2.50 (m, 1H), 2.00 (m, 2H), 1.80 (m, 3H), 1.50-1.30 (m, 2H). |
| 16 | 128-129 | 400 MHz; | DMSO d6 | δ (ppm): 9.35 (s, 1H), 9.10 (d, 1H), 8.30 (d, 1H), 7.40 (m, 1H), 7.25 (s, 1H), 7.20 (m, 1H), 7.05 (m, 1H), 5.00 (dd, 1H), 3.75 (ddd, 1H), 3.25 (m, 1H), 2.75 (m, 2H), 2.50 (m, 1H), 2.00 (m, 2H), 1.80 (m, 3H), 1.50-1.30 (m, 2H). |
| 17 | 172-176 | 400 MHz; | DMSO d6 | δ (ppm): 9.35 (s, 1H), 9.00 (dd, 1H), 8.15 (dd, 1H), 7.40-7.10 (m, 6H), 4.95 (dd, 1H), 4.80 (dd, 1H), 4.40 (m, 1H), 3.75 (m, 1H), 3.30 (m, 1H), 2.90 (m, 1H), 2.75 (m, 1H), 2.25 (dd, 1H), 1.90 (m, 2H), 1.70 (m, 1H), 1.60-1.30 (m, 2H). |
| 18 | 118-119 | 400 MHz; | DMSO d6 | δ (ppm): 9.35 (s, 1H), 9.10 (d, 1H), 8.25 (d, 1H), 7.25 (s, 1H), 4.90 (d, 1H), 3.90 (ddd, 1H), 3.10 (m, 1H), 2.60 (m, 1H), 2.10-1.50 (m, 11H), 1.40-1.10 (m, 3H). |
| 19 | 206-209 | 400 MHz; | DMSO d6 | δ (ppm): 9.35 (s, 1H), 9.00 (dd, 1H), 8.15 (dd, 1H), 7.40-7.10 (m, 6H), 5.45 (m, 1H), 5.00 (d, 1H), 3.75 (m, 2H), 3.65 (m, 1H), 3.10 (m, 1H), 2.20 (m, 1H), 2.00-1.70 (m, 3H), 1.60-1.30 (m, 2H). |
| 20 | 139-140 | 400 MHz; | DMSO d6 | δ (ppm): 9.45 (s, 1H), 9.08 (d, 1H), 8.25 (d, 1H), 7.32 (s, 1H), 5.71 (m, 1H), 5.01 (m, 1H), 3.98 (m, 1H), 2.23 (m, 2H), 1.98-1.87 (m, 3H), 1.55 (m, 1H). |
| 21 | 172-176 | 400 MHz; | DMSO d6 | δ (ppm): 9.35 (s, 1H), 9.00 (m, 1H), 8.15 (m, 1H), 7.25 (s, 1H), 7.15 (m, 2H), 6.70 (d, 2H), 5.00 (m, 1H), 3.75 (s, 1H), 3.65 (m, 5H), 3.40 (m, 2H), 2.10 (m, 1H), 1.90 (m, 1H), 1.70-1.40 (m, 4H). |
| 22 | 126-128 | 400 MHz; | DMSO d6 | δ (ppm): 9.35 (s, 1H), 9.10 (d, 1H), 8.00 (d, 1H), 7.22 (s, 1H), 4.98 (m, 1H), 4.70 (m, 1H), 4.40 (m, 1H), 3.80 (m, 1H), 3.30-3.00 (m, 1H), 2.35-2.10 (m, 1H), 2.00-1.60 (m, 3H), 1.40-1.20 (m, 5H). |
| 23 | 156-158 | 400 MHz; | DMSO d6 | δ (ppm): 9.35 (s, 1H), 9.10 (d, 1H), 8.20 (d, 1H), 7.25 (s, 1H), 5.60-5.30 (m, 1H), 5.00 (m, 1H), 3.80-3.60 (m, 2H), 2.00 (m, 2H), 1.90-1.70 (m, 2H), 1.65-1.30 (m, 5H). |
| 24 | 203-205 | 400 MHz; | DMSO d6 | δ (ppm): 9.32 (s, 1H), 9.02 (d, 1H), 8.31 (d, 1H), 7.45 (m, 2H), 7.22 (s, 1H), 7.11 (m, 2H), 5.00 (m, 1H), 3.80 (m, 1H), 3.65 (m, 1H), 3.47 (m, 1H), 2.90 (m, 1H), 1.97 (m, 1H), 1.80 (m, 2H), 1.61 (m, 1H), 1.38 (m, 2H). |
| 25 | 105-110 | 400 MHz; | DMSO d6 | δ (ppm): 9.35 (m, 1H), 9.00 (m, 1H), 8.25 (m, 1H), 7.40-7.10 (m, 6H), 5.10 (m, 1H), 4.80-4.10 (m, 3H), 3.00-2.60 (m, 1H), 2.30 (m, 1H), 1.90-1.40 (m, 9H). |
| 26 | 174-175 | 400 MHz; | DMSO d6 | δ (ppm): 9.32 (s, 1H), 9.02 (d, 1H), 8.31 (d, 1H), 7.45 (m, 2H), 7.22 (s, 1H), 7.11 (m, 2H), 5.00 (m, 1H), 3.80 (m, 1H), 3.65 (m, 1H), 3.47 (m, 1H), 2.90 (m, 1H), 1.97 (m, 1H), 1.80 (m, 2H), 1.61 (m, 1H), 1.38 (m, 2H). |
| 27 | 174-175 | 400 MHz; | DMSO d6 | δ (ppm): 9.32 (s, 1H), 9.02 (d, 1H), 8.31 (d, 1H), 7.45 (m, 2H), 7.22 (s, 1H), 7.11 (m, 2H), 5.00 (m, 1H), 3.80 (m, 1H), 3.65 (m, 1H), 3.47 (m, 1H), 2.90 (m, 1H), 1.97 (m, 1H), 1.80 (m, 2H), 1.61 (m, 1H), 1.38 (m, 2H). |

A list of chemical structures and physical data for compounds of the aforementioned formula (I), illustrating the present invention, is given in table 3. The compounds have been prepared according to the methods of the examples.

In the table 3, m represents 2, Me represents a methyl group, Et represents a ethyl group, (Rot.) indicates the levorotatory or dextrorotatory properties of the enantiomeric compound, (dec.) indicates the decomposition of the compound. Table 3A provides analytic data for the compounds of table 3.

TABLE 3

Formula (I): bicyclic core with substituents R1, R2, R3, R4, X, and (CH2)m.

| No. | Rot | R3 | R1 | R4 | R2 | X | salt |
|---|---|---|---|---|---|---|---|
| 1 | (+/−) | ethyl | 4-methylpyrimidin-2-yl | H | H | N—CO₂Et | Free base |
| 2 | (+/−) | ethyl | 4-methylpyrimidin-2-yl | H | H | NH | Hydrobromide (1:1) |
| 3 | (+/−) | phenylpropyl | 4-methylpyrimidin-2-yl | H | H | NH | Hydrochloride (1:1) |
| 4 | (+/−) | 2-(4-fluorophenyl)ethyl | 4-methylpyrimidin-2-yl | H | H | N—CO₂Et | Free base |

TABLE 3A

| N° | Mp ° C. | | NMR |
|---|---|---|---|
| 1 | 160-162 | 400 MHz DMSO d6 | δ (ppm): 9.32 (s, 1H), 9.08 (d, 1H), 8.28 (d, 1H), 7.30 (s, 1H), 4.88 (m, 1H), 4.05 (m, 3H), 3.91 (m, 2H), 3.41 (m, 1H), 3.30 (m, 2H), 2.12 (m, 1H), 1.68 (m, 1H), 1.18 (t, 3H), 1.08 (t, 3H). |
| 2 | 278-280 | 400 MHz DMSO d6 | δ (ppm): 9.38 (s, 1H), 9.20 (br s, 1H), 9.10 (d, 1H), 8.28 (d, 1H), 7.32 (s, 1H), 5.18 (m, 1H), 4.10 (m, 1H), 3.67 (m, 1H), 3.48 (m, 2H), 3.18 (m, 2H), 2.26 (m, 1H), 1.69 (m, 1H), 1.10 (t, 3H). |
| 3 | 288-290 | 400 MHz DMSO d6 | δ (ppm): 9.60 (br s, 1H), 9.35 (s, 1H), 9.10 (d, 1H), 8.25 (d, 1H), 7.40-7.10 (m, 6H), 5.20 (dd, 1H), 4.10 (ddd, 1H), 3.80-3.50 (m, 3H), 3.25 (m, 2H), 2.80 (m, 2H), 2.50 (m, 1H), 1.90 (m, 1H). |
| 4 | 203-205 | 400 MHz DMSO d6 | δ (ppm): 9.32 (s, 1H), 9.08 (d, 1H), 8.28 (d, 1H), 7.40 (m, 2H), 7.25 (s, 1H), 7.10 (m, 2H), 4.90 (m, 1H), 4.05 (m, 1H), 3.90 (m, 3H), 3.75 (m, 1H), 3.50-3.30 (m, 3H), 3.00 (m, 2H), 1.08 (t, 3H). |

Test Example: Inhibitory Activity of the Medicament of the Present Invention Against GSK3β

Four different protocols can be used.

In a first protocol: 7.5 μM of prephosphorylated GS1 peptide and 10 μM ATP (containing 300,000 cpm of ³³P-ATP) were incubated in 25 mM Tris-HCl, pH 7.5, 0.6 mM DTT, 6 mM MgCl₂, 0.6 mM EGTA, 0.05 mg/ml BSA buffer for 1 hour at room temperature in the presence of GSK3beta (total reaction volume: 100 microliters).

In a second protocol: 4.1 µM of prephosphorylated GS1 peptide and 42 µM ATP (containing 260,000 cpm $^{33}$P-ATP) were incubated in 80 mM Mes-NaOH, pH 6.5, 1 mM Mg acetate, 0.5 mM EGTA, 5 mM 2-mercaptoethanol, 0.02% Tween 20, 10% glycerol buffer for 2 hours at room temperature in the presence of GSK3beta.

In a third protocol: 7.5 µM of prephosphorylated GS1 peptide and 10 µM ATP (containing 300,000 cpm of $^{33}$P-ATP) were incubated in 50 mM Hepes, pH 7.2, 1 mM DTT, 1 mM MgCl$_2$, 1 mM EGTA, 0.01% Tween 20 buffer for one hour at room temperature in the presence of GSK3beta (total reaction volume: 100 microliters).

In a fourth protocol: 7.5 µM of prephosphorylated GS1 peptide and 10 µM ATP (containing 300,000 cpm of $^{33}$P-ATP) were incubated in 50 mM Hepes, pH 7.2, 1 mM DTT, 1 mM MgCl$_2$, 1 mM EGTA, 0.01% Tween 20 buffer for 90 minutes at room temperature in the presence of commercial GSK3beta (Millipore) (total reaction volume: 100 microliters).

Inhibitors were solubilized in DMSO (final solvent concentration in the reaction medium, 1%).

The reaction was stopped with 100 microliters of a solution made of 25 g polyphosphoric acid (85% P$_2$O$_5$), 126 ml 85% H$_3$PO$_4$, H$_2$O to 500 ml and then diluted to 1:100 before use. An aliquot of the reaction mixture was then transferred to Whatman P81 cation exchange filters and rinsed with the solution described above. Incorporated $^{33}$P radioactivity was determined by liquid scintillation spectrometry.

The phosphorylated GS-1 peptide had the following sequence: NH2-YRRAAVPPSPSLSRHSSPHQS(P)EDEE-COOH. (Woodgett, J. R. (1989) Analytical Biochemistry 180, 237-241.

The GSK3β inhibitory activity of the compounds of the present invention are expressed in IC$_{50}$, and as an illustration the range of IC$_{50}$'s of the compounds in table 1 are between 0.1 nanomolar to 3 micromolar concentrations.

For example, on the protocol 4, the compound No 20 of table 2 shows an IC$_{50}$ of 0.008 µM. The compound No 1 of table 3 shows an inhibition of 63% at 1 µM.

Formulation Example (1) Tablets

The ingredients below were mixed by an ordinary method and compressed by using a conventional apparatus.

| | |
|---|---|
| Compound of Example 1 | 30 mg |
| Crystalline cellulose | 60 mg |
| Corn starch | 100 mg |
| Lactose | 200 mg |
| Magnesium stearate | 4 mg |

(2) Soft Capsules

The ingredients below were mixed by an ordinary method and filled in soft capsules.

| | |
|---|---|
| Compound of Example 1 | 30 mg |
| Olive oil | 300 mg |
| Lecithin | 20 mg |

(3) Parenteral Preparations

The ingredients below were mixed by an ordinary method to prepare injections contained in a 1 ml ampoule.

| | |
|---|---|
| Compound of Example 1 | 3 mg |
| Sodium chloride | 4 mg |
| Distilled water for injection | 1 ml |

Industrial Applicability

The compounds of the present invention have GSK3β inhibitory activity and are useful as an active ingredient of a medicament for preventive and/or therapeutic treatment of diseases caused by abnormal activity of GSK3β and more particularly of neurodegenerative diseases.

What is claimed is:

1. A compound of formula (I):

(I)

wherein:
X represents a methylene, NH, or a nitrogen atom substituted by a C(O)—O—(C$_{1-6}$-alkyl) group;
R1 represents a 2, 3 or 4-pyridine ring or a 2, 4 or 5-pyrimidine ring, the ring being optionally substituted by a C$_{1-6}$ alkyl group, a C$_{1-6}$ alkoxy group or a halogen atom;
R2 represents a hydrogen atom, a C$_{1-6}$ alkyl group or a halogen atom;
R3 represents a C$_{1-6}$ alkyl group which is optionally substituted by 1 to 4 substituents selected from the group consisting of a halogen atom, a hydroxyl group, a C$_{1-6}$ alkoxy group, a C$_{1-2}$ perhalogenated alkyl group, a C$_{1-3}$ halogenated alkyl group, C$_{1-6}$ alkyl group, and an aromatic group, wherein the aromatic group is optionally substituted by 1 to 4 substituents selected from a halogen atom, a hydroxyl group, a C$_{1-6}$ alkoxy group, and a C$_{1-6}$ alkyl group;
R4 represents a hydrogen atom, a halogen atom, a hydroxyl group, or a C$_{1-6}$ alkyl group; and
m represents 1 to 2 when X is a methylene or
m represents 2 when X is NH or a nitrogen atom substituted by a C(O)—O—(C$_{1-6}$-alkyl) group;
or an acid addition salt thereof.

2. The compound of formula (I) according to claim 1:

(I)

wherein
X represents a methylene, NH, or a nitrogen atom substituted by a C(O)—O—(C$_{1-6}$-alkyl) group;
R1 represents an unsubstituted 4-pyridine ring or an unsubstituted 4-pyrimidine ring;
R2 represents a hydrogen atom;
R3 represents a C$_{1-6}$ alkyl group which is optionally substituted by 1 to 4 substituents selected from the group consisting of a halogen atom, a hydroxyl group, a $C_{1-2}$ perhalogenated alkyl group, $C_{1-6}$ alkyl group, and a phenyl group wherein the phenyl group is optionally substituted by 1 to 4 substituents selected from a halogen atom and a $C_{1-6}$alkoxy group;

R4 represents a hydrogen atom;

m represents 1 to 2 when X is a methylene, or m represents 2 when X is NH or a nitrogen atom substituted by a C(O)—O—($C_{1-6}$-alkyl) group;

or an acid addition salt thereof.

3. The compound according to claim 1 selected from the group consisting of:

(+/−)-9-[2-(2-Methoxy-phenyl)-ethyl]-2-pyridin-4-yl-6,7,8,9-tetrahydro-pyrido[1,2-α]pyrimidin-4-one;
(+/−)-9-(3-Chloro-benzyl)-2-pyrimidin-4-yl-6,7,8,9-tetrahydro-pyrido[1,2-α]pyrimidin-4-one;
(+/−)-9-(4-Fluoro-benzyl)-2-pyrimidin-4-yl-6,7,8,9-tetrahydro-pyrido[1,2-α]pyrimidin-4-one;
(+/−)-9-(5-Bromo-2-methoxy-benzyl)-2-pyrimidin-4-yl-6,7,8,9-tetrahydro-pyrido[1,2-α]pyrimidin-4-one;
(+/−)-10-Methyl-2-pyrimidin-4-yl-7,8,9,10-tetrahydro-6H-pyrimido[1,2-α]azepin-4-one;
(+/−)-10-Methyl-2-pyridin-4-yl-7,8,9,10-tetrahydro-6H-pyrimido[1,2-α]azepin-4-one;
(+/−)-10-Ethyl-2-pyrimidin-4-yl-7,8,9,10-tetrahydro-6H-pyrimido[1,2-α]azepin-4-one;
(+/−)-10-Ethyl-2-pyridin-4-yl-7,8,9,10-tetrahydro-6H-pyrimido[1,2-α]azepin-4-one;
(+/−)-10-(2-(Phenyl-ethyl)-2-pyrimidin-4-yl-7,8,9,10-tetrahydro-6H-pyrimido[1,2-α]azepin-4-one;
(+/−)-10-Benzyl-2-pyrimidin-4-yl-7,8,9,10-tetrahydro-6H-pyrimido[1,2-α]azepin-4-one;
(+/−)-10-(3-Phenyl-propyl)-2-pyrimidin-4-yl-7,8,9,10-tetrahydro-6H-pyrimido[1,2-α]azepin-4-one;
(+/−)-10-[(4-Fluoro-2-methoxy-phenyl)-hydroxy-methyl]-2-pyrimidin-4-yl-7,8,9,10-tetrahydro-6H-pyrimido[1,2-α]azepin-4-one;
(+/−)-10-[2-(3,4-Dimethoxy-phenyl)-ethyl]-2-pyrimidin-4-yl-7,8,9,10-tetrahydro-6H-pyrimido[1,2-α]azepin-4-one;
(+/−)-10-[Fluoro-(4-fluoro-2-methoxy-phenyl)methyl]-2-pyrimidin-4-yl-7,8,9,10-tetrahydro-6H-pyrimido[1,2-α]azepin-4-one;
(+/−)-10-[2-(4-Methoxy-phenyl)ethyl]-2-pyrimidin-4-yl-7,8,9,10-tetrahydro-6H-pyrimido[1,2-α]azepin-4-one;
(+/−)-10-[2-(2-Methoxy-phenyl)-ethyl]-2-pyrimidin-4-yl-7,8,9,10-tetrahydro-6H-pyrimido[1,2-α]azepin-4-one;
(+/−)-10-(2-Methyl-2-phenyl-propyl)-2-pyrimidin-4-yl-7,8,9,10-tetrahydro-6H-pyrimido[1,2-α]azepin-4-one;
(+/−)-10-Isobutyl-2-pyrimidin-4-yl-7,8,9,10-tetrahydro-6H-pyrimido[1,2-α]azepin-4-one;
(+/−)-10-[2-(4-Fluoro-2-methoxy-phenyl)-ethyl]-2-pyrimidin-4-yl-7,8,9,10-tetrahydro-6H-pyrimido[1,2-α]azepin-4-one;
(+/−)-10-[2-(2,4-Difluoro-phenyl)-ethyl]-2-pyrimidin-4-yl-7,8,9,10-tetrahydro-6H-pyrimido[1,2-α]azepin-4-one;
(+/−)-10-(1-Hydroxy-2-phenyl-ethyl)-2-pyrimidin-4-yl-7,8,9,10-tetrahydro-6H-pyrimido[1,2-α]azepin-4-one;
(+/−)-10-Cyclopentyl-2-pyrimidin-4-yl-7,8,9,10-tetrahydro-6H-pyrimido[1,2-α]azepin-4-one;
(+/−)-10-(1-Fluoro-2-phenyl-ethyl)-2-pyrimidin-4-yl-7,8,9,10-tetrahydro-6H-pyrimido[1,2-α]azepin-4-one;
(+/−)-10-Cyclopropyl-2-pyrimidin-4-yl-7,8,9,10-tetrahydro-6H-pyrimido[1,2-α]azepin-4-one;
(+/−)-2-Pyrimidin-4-yl-10-[2,2,2-trifluoro-1-hydroxy-1-(4-methoxy-benzyl)-ethyl]-7,8,9,10-tetrahydro-6H-pyrimido[1,2-α]azepin-4-one;
(+/−)-10-(1-Hydroxy-ethyl)-2-pyrimidin-4-yl-7,8,9,10-tetrahydro-6H-pyrimido[1,2-α]azepin-4-one;
(+/−)-10-(1-Fluoro-ethyl)-2-pyrimidin-4-yl-7,8,9,10-tetrahydro-6H-pyrimido[1,2-α]azepin-4-one;
(+/−)-10-(4-Fluoro-benzyl)-2-pyrimidin-4-yl-7,8,9,10-tetrahydro-6H-pyrimido[1,2-α]azepin-4-one;
(+/−)-10-(1-Hydroxy-2-phenyl-ethyl)-10-methyl-2-pyrimidin-4-yl-7,8,9,10-tetrahydro-6H-pyrimido[1,2-α]azepin-4-one;
(+)-10-(4-Fluoro-benzyl)-2-pyrimidin-4-yl-7,8,9,10-tetrahydro-6H-pyrimido[1,2-α]azepin-4-one;
(−)-10-(4-Fluoro-benzyl)-2-pyrimidin-4-yl-7,8,9,10-tetrahydro-6H-pyrimido[1,2-α]azepin-4-one;
(+/−)-9-Ethyl-4-oxo-2-pyrimidin-4-yl-5,6,8,9-tetrahydro-4H-1,4-a,7-triaza-benzocycloheptene-7-carboxylic acid ethyl ester;
(+/−)-9-Ethyl-2-pyrimidin-4-yl-6,7,8,9-tetrahydro-5H-1,4-a,7-triaza-benzocyclohepten-4-one;
(+/−)-9-(2-Phenyl-ethyl)-2-pyrimidin-4-yl-6,7,8,9-tetrahydro-5H-1,4-a,7-triaza-benzocyclohepten-4-one; and
(+/−)-9-(4-Fluoro-benzyl)-4-oxo-2-pyrimidin-4-yl-5,6,8,9-tetrahydro-4H-1,4-a,7-triaza-benzocycloheptene-7-carboxylic acid ethyl ester;

or an acid addition salt thereof.

4. A compound of formula (II) or formula (V):

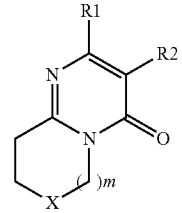

(II)

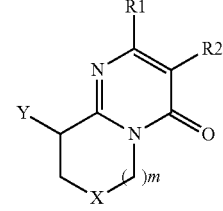

(V)

wherein:

X represents NH or a nitrogen atom substituted by a C(O)—O—($C_{1-6}$-alkyl) group;

R1 represents an 4-pyridine ring or an 4-pyrimidine ring;

R2 represents a hydrogen atom; and

Y represents a halogen.

5. A pharmaceutical composition comprising a compound of formula (I) according to claim 1 or a pharmaceutically acceptable salt, hydrate or solvate thereof and one or more pharmaceutical additives.

6. A pharmaceutical composition comprising a compound of formula (I) according to claim 2 or a pharmaceutically acceptable salt, hydrate or solvate thereof and one or more pharmaceutical additives.

7. A pharmaceutical composition comprising a compound according to claim 3 or a pharmaceutically acceptable salt, hydrate or solvate thereof and one or more pharmaceutical additives.

8. A method of inhibiting the activity of glycogen synthase kinase 3-beta (GSK3-β), which comprises administering to a patient in need of said inhibition a therapeutically effective amount of a compound of formula (I) according to claim 1 or a pharmaceutically acceptable salt thereof.

9. A method of treating malaria in a patient, comprising administering to said patient a therapeutically effective amount of a compound of formula (I) according to claim 1 or a pharmaceutically acceptable salt thereof.

10. A method of treating *Pemphigus vulgaris* in a patient, comprising administering to said patient a therapeutically effective amount of a compound of formula (I) according to claim 1 or a pharmaceutically acceptable salt thereof.

11. A process for the synthesis of the compound of formula (I):

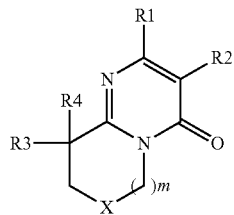

according to claim 2, comprising reacting a compound of formula (II)

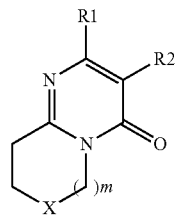

with R4-L and then R3-A, wherein R3 and R4 are as defined in claim 2; L represents a tosyl, mesyl or bromine, A represents a tosyl, mesyl or halogen, R1 represents an 4-pyridine ring or an 4-pyrimidine ring; and R2 represents a hydrogen atom.

* * * * *